(12) United States Patent
Sverdlov et al.

(10) Patent No.: US 12,290,701 B2
(45) Date of Patent: May 6, 2025

(54) HEAD WEARABLE LIGHT THERAPY DEVICE

(71) Applicant: JelikaLite LLC, New York, NY (US)

(72) Inventors: Katya Sverdlov, New York, NY (US); Eugenia Steingold, New York, NY (US); David Conroy, New York, NY (US)

(73) Assignee: JelikaLite LLC, New York, NY (US)

( * ) Notice: Subject to any disclaimer, the term of this patent is extended or adjusted under 35 U.S.C. 154(b) by 0 days.

(21) Appl. No.: 18/212,153

(22) Filed: Jun. 20, 2023

(65) Prior Publication Data
US 2024/0325779 A1    Oct. 3, 2024

Related U.S. Application Data

(63) Continuation of application No. 17/769,708, filed as application No. PCT/US2020/055782 on Oct. 15, 2020.

(Continued)

(51) Int. Cl.
*A61N 5/06* (2006.01)
*A61B 5/372* (2021.01)

(52) U.S. Cl.
CPC ............ *A61N 5/0622* (2013.01); *A61B 5/372* (2021.01); *A61N 2005/0626* (2013.01); *A61N 2005/0628* (2013.01); *A61N 2005/0647* (2013.01); *A61N 2005/0652* (2013.01); *A61N 2005/0659* (2013.01); *A61N 2005/0663* (2013.01)

(58) Field of Classification Search
CPC .......... A61N 5/0618; A61N 2005/0632; A61N 2005/0647; A61N 2005/0652; A61N 2005/0659; A61N 2005/0663; A61N 2005/0626; A61N 5/0622;
(Continued)

(56) References Cited

U.S. PATENT DOCUMENTS

D192,070 S    1/1962  Wall
D284,080 S    6/1986  Swezey et al.
(Continued)

FOREIGN PATENT DOCUMENTS

CN    113559420 A    10/2021
EP    1040398 A2    10/2000
(Continued)

OTHER PUBLICATIONS

U.S. Appl. No. 18/111,258, filed Feb. 17, 2023, Pending.
(Continued)

*Primary Examiner* — Jonathan T Kuo
(74) *Attorney, Agent, or Firm* — McCarter & English, LLP

(57) ABSTRACT

Systems and methods are described for treatment of neurological conditions in which transcranial illumination using infrared, near-infrared and/or red wavelengths of light are delivered into the brain of a patient using a portable head wearable device. Arrays of light emitters are simultaneously controlled to provide a selected power density and distribution during a therapeutic session to treat a condition of the patient. An external controller such as a touchscreen tablet or laptop computer can be used to select illumination parameters for each patient. The system can be used to provide treatment to children such as those having autism spectrum disorder (ASD).

20 Claims, 19 Drawing Sheets

Related U.S. Application Data

(60) Provisional application No. 63/033,756, filed on Jun. 2, 2020, provisional application No. 62/940,788, filed on Nov. 26, 2019, provisional application No. 62/915,221, filed on Oct. 15, 2019.

(58) Field of Classification Search
CPC ....... A61N 2005/0662; A61N 5/06–2005/073; G16H 10/60; G16H 40/63; G16H 20/40
See application file for complete search history.

(56) References Cited

U.S. PATENT DOCUMENTS

| | | |
|---|---|---|
| D293,373 S | 12/1987 | Beck |
| 6,273,905 B1 | 8/2001 | Streeter |
| 6,702,837 B2 | 3/2004 | Gutwein |
| 6,785,568 B2 | 8/2004 | Chance |
| 7,303,578 B2 | 12/2007 | De Taboada et al. |
| 7,309,348 B2 | 12/2007 | Streeter et al. |
| 7,316,922 B2 | 1/2008 | Streeter |
| 7,354,432 B2 | 4/2008 | Eells et al. |
| 7,534,255 B1 | 5/2009 | Streeter et al. |
| 7,575,589 B2 | 8/2009 | De Taboada et al. |
| 7,947,067 B2 | 5/2011 | Tucek et al. |
| 8,025,687 B2 | 9/2011 | Streeter et al. |
| 8,165,684 B2 | 4/2012 | Putz et al. |
| 8,167,921 B2 | 5/2012 | Streeter et al. |
| 8,308,784 B2 | 11/2012 | Streeter et al. |
| 8,366,756 B2 | 2/2013 | Tucek et al. |
| 8,371,716 B2 | 2/2013 | Shen et al. |
| 8,374,696 B2 | 2/2013 | Sanchez et al. |
| 8,409,264 B2 | 4/2013 | Shanks et al. |
| 8,439,959 B2 | 5/2013 | Tucek et al. |
| 8,813,756 B1 | 8/2014 | Shanks et al. |
| 8,814,924 B2 | 8/2014 | Shanks et al. |
| 8,932,338 B2 | 1/2015 | Lim et al. |
| 8,961,415 B2 | 2/2015 | LeBoeuf et al. |
| 9,149,650 B2 | 10/2015 | Shanks et al. |
| D746,516 S | 12/2015 | Cardello et al. |
| D747,696 S | 1/2016 | Hardi |
| 9,510,765 B2 | 12/2016 | Greder |
| D778,544 S | 2/2017 | Slye, Jr. |
| 9,795,803 B2 | 10/2017 | Streeter et al. |
| D819,823 S | 6/2018 | Pelletier |
| 9,993,659 B2 | 6/2018 | Streeter et al. |
| 10,068,490 B2 | 9/2018 | Hibbs et al. |
| 10,071,259 B2 | 9/2018 | DeLapp et al. |
| D833,119 S | 11/2018 | Yates |
| 10,188,872 B2 | 1/2019 | De Taboada et al. |
| 10,272,259 B1 | 4/2019 | Blanche |
| 10,315,042 B2 | 6/2019 | De Taboada et al. |
| 10,357,662 B2 | 7/2019 | De Taboada et al. |
| 10,384,076 B2 | 8/2019 | Wagenaar Cacciola et al. |
| D870,062 S | 12/2019 | Peng |
| 10,653,889 B2 | 5/2020 | De Taboada et al. |
| 10,683,494 B2 | 6/2020 | Streeter et al. |
| 10,695,577 B2 | 6/2020 | De Taboada et al. |
| 10,695,579 B2 | 6/2020 | De Taboada et al. |
| D889,676 S | 7/2020 | Chen |
| D894,413 S | 8/2020 | Kim |
| D897,549 S | 9/2020 | Park et al. |
| 10,758,743 B2 | 9/2020 | De Taboada et al. |
| 10,780,296 B2 | 9/2020 | Zivin et al. |
| 10,857,376 B2 | 12/2020 | De Taboada et al. |
| 10,913,943 B2 | 2/2021 | Streeter et al. |
| 11,179,572 B2 | 11/2021 | Taboada et al. |
| 11,213,250 B2 | 1/2022 | Goldstein et al. |
| 11,219,782 B2 | 1/2022 | Taboada et al. |
| 11,273,319 B2 | 3/2022 | De Taboada et al. |
| D949,355 S | 4/2022 | Steingold et al. |
| 11,633,621 B2 * | 4/2023 | Lim ..................... A61B 5/0075 607/92 |
| 11,857,801 B2 | 1/2024 | Devens et al. |
| 11,986,667 B2 * | 5/2024 | Sverdlov ................ G16H 40/63 |
| 2003/0018961 A1 | 1/2003 | Ogasawara |
| 2003/0109906 A1 | 6/2003 | Streeter |
| 2003/0125782 A1 | 7/2003 | Streeter |
| 2003/0144712 A1 | 7/2003 | Streeter |
| 2003/0181861 A1 | 9/2003 | Wilkinson |
| 2003/0181962 A1 | 9/2003 | Streeter |
| 2003/0212442 A1 | 11/2003 | Streeter |
| 2004/0132002 A1 | 7/2004 | Streeter |
| 2004/0153130 A1 | 8/2004 | Oron et al. |
| 2004/0220513 A1 | 11/2004 | Streeter |
| 2005/0009161 A1 | 1/2005 | Streeter |
| 2005/0159793 A1 | 7/2005 | Streeter |
| 2005/0177093 A1 | 8/2005 | Barry et al. |
| 2006/0079773 A1 | 4/2006 | Mourad et al. |
| 2006/0161226 A1 | 7/2006 | McMickle |
| 2006/0167531 A1 | 7/2006 | Gertner et al. |
| 2006/0223155 A1 | 10/2006 | Streeter |
| 2007/0150027 A1 | 6/2007 | Rogers |
| 2007/0179570 A1 | 8/2007 | De Taboada et al. |
| 2007/0191727 A1 | 8/2007 | Fadem |
| 2007/0233208 A1 | 10/2007 | Kurtz et al. |
| 2008/0221211 A1 | 9/2008 | Streeter |
| 2009/0012586 A1 | 1/2009 | Kepecs |
| 2009/0157141 A1 | 6/2009 | Chiao et al. |
| 2011/0015707 A1 | 1/2011 | Tucker et al. |
| 2011/0105909 A1 | 5/2011 | Sun et al. |
| 2011/0160814 A2 | 6/2011 | Tucker et al. |
| 2011/0251658 A1 | 10/2011 | Chen et al. |
| 2012/0065709 A1 | 3/2012 | Dunning et al. |
| 2012/0289869 A1 | 11/2012 | Tyler |
| 2013/0041432 A1 | 2/2013 | Tucker et al. |
| 2013/0090520 A1 | 4/2013 | Redfield et al. |
| 2013/0178731 A1 | 7/2013 | Bosl |
| 2013/0304019 A1 | 11/2013 | Cooper et al. |
| 2015/0112411 A1 | 4/2015 | Beckman et al. |
| 2015/0209597 A1 | 7/2015 | Haarlander et al. |
| 2015/0246240 A1 | 9/2015 | Huttemann |
| 2015/0374971 A1 | 12/2015 | Dar et al. |
| 2016/0235983 A1 * | 8/2016 | Berman ................ A61N 2/006 |
| 2016/0367834 A1 | 12/2016 | Sauer |
| 2017/0028216 A1 | 2/2017 | Medendorp, Jr. et al. |
| 2017/0143228 A1 | 5/2017 | Leuthardt, Jr. et al. |
| 2017/0165485 A1 | 6/2017 | Sullivan et al. |
| 2017/0290524 A1 | 10/2017 | Jiang et al. |
| 2018/0133504 A1 | 5/2018 | Malchano et al. |
| 2018/0169434 A1 | 6/2018 | Shanks |
| 2018/0169435 A1 | 6/2018 | Shanks |
| 2018/0169436 A1 | 6/2018 | Shanks |
| 2018/0322801 A1 | 11/2018 | Dey et al. |
| 2019/0060662 A1 | 2/2019 | Pina |
| 2019/0069796 A1 | 3/2019 | Santello et al. |
| 2019/0070431 A1 | 3/2019 | Zivin et al. |
| 2019/0078073 A1 | 3/2019 | Streeter et al. |
| 2019/0143114 A1 | 5/2019 | Nelson |
| 2019/0262626 A1 | 8/2019 | De Taboada et al. |
| 2019/0299021 A1 | 10/2019 | Kamei |
| 2020/0033078 A1 | 1/2020 | Lindstroem |
| 2020/0069959 A1 | 3/2020 | Johnson et al. |
| 2020/0086138 A1 | 3/2020 | Cassano |
| 2020/0109847 A1 | 4/2020 | Poggio et al. |
| 2020/0187857 A1 | 6/2020 | Jovanovic et al. |
| 2020/0230434 A1 | 7/2020 | Tajkef et al. |
| 2020/0269065 A1 | 8/2020 | Broeng et al. |
| 2020/0289054 A1 | 9/2020 | Muvvala |
| 2020/0298014 A1 | 9/2020 | Stasko et al. |
| 2020/0330786 A1 | 10/2020 | De Taboada et al. |
| 2020/0360715 A1 * | 11/2020 | Lim ..................... A61N 5/0622 |
| 2021/0015393 A1 | 1/2021 | Jordan et al. |
| 2021/0113853 A1 | 4/2021 | Devens et al. |
| 2021/0205634 A1 | 7/2021 | Sverdlov et al. |
| 2021/0353957 A1 | 11/2021 | Telfer et al. |
| 2022/0126114 A1 | 4/2022 | De Taboada et al. |
| 2022/0152415 A1 | 5/2022 | De Taboada et al. |
| 2022/0193443 A1 | 6/2022 | De Taboada et al. |
| 2022/0387818 A1 * | 12/2022 | Sverdlov ............. A61N 5/0622 |
| 2023/0092770 A1 | 3/2023 | Steingold et al. |

(56) References Cited

U.S. PATENT DOCUMENTS

| | | | |
|---|---|---|---|
| 2023/0285772 | A1* | 9/2023 | Sverdlov .............. A61N 5/0618 |
| 2024/0293679 | A1 | 9/2024 | Sverdlov et al. |

FOREIGN PATENT DOCUMENTS

| | | | |
|---|---|---|---|
| JP | 2017-006742 A | 1/2017 | |
| JP | 2017-192812 A | 10/2017 | |
| JP | 2019-520170 A | 7/2019 | |
| WO | 1999/31560 A2 | 6/1999 | |
| WO | 2008/029001 A1 | 3/2008 | |
| WO | 2008/144157 A1 | 11/2008 | |
| WO | 2009/117323 A2 | 9/2009 | |
| WO | 2011/011334 A2 | 1/2011 | |
| WO | 2012/024243 A1 | 2/2012 | |
| WO | 2012/130958 A1 | 10/2012 | |
| WO | 2013/036558 A1 | 3/2013 | |
| WO | 2015/069627 A1 | 5/2015 | |
| WO | 2016/127183 A1 | 8/2016 | |
| WO | 2017/013051 A1 | 1/2017 | |
| WO | 2017/019839 A1 | 2/2017 | |
| WO | 2018/018019 A1 | 1/2018 | |
| WO | 2018/051354 A1 | 3/2018 | |
| WO | 2018/109715 A1 | 6/2018 | |
| WO | 2018/133504 A1 | 7/2018 | |
| WO | 2018/152255 A1 | 8/2018 | |
| WO | 2019/053625 A1 | 3/2019 | |
| WO | 2020/250160 A1 | 12/2020 | |
| WO | 2021/076756 A1 | 4/2021 | |
| WO | 2022/010952 A1 | 1/2022 | |
| WO | 2022/197937 A1 | 9/2022 | |

OTHER PUBLICATIONS

U.S. Appl. No. 17/105,313, filed Nov. 25, 2020, 2021-0205634, Published.
Antonucci et al., Manual Lymphatic Drainage in Autism Treatment. Madridge Journal of Immunology. 2018;3(1):69-72.
Bogdanova et al., LED Therapy Improves Sleep and Cognition in Chronic Moderate TBI: Pilot Case Studies. Journal of Head Trauma Rehabilitation. May 2015;e77:Poster 235. 1 page.
Cassano et al., Near-Infrared Transcranial Radiation for Major Depressive Disorder: Proof of Concept Study. Psychiatry J. 2015;2015:352979.
Chambon et al., A Deep Learning Architecture to Detect Events in EEG Signals During Sleep. IEEE 28th International Workshop on Machine Learning for Signal Processing (MLSP). 5 pages, (2018).
Coyle et al., Brain-computer interface using a simplified functional near-infrared spectroscopy system. J Neural Eng. 2007;4:219-226.
Delye et al., Creating a normative database of age-specific 3D geometrical data, bone density, and bone thickness of the developing skull: a pilot study. J Neurosurg Pediatr. 2015; 16:687-702.
Grossi et al., Detection of an Autism EEG Signature From Only Two EEG Channels Through Features Extraction and Advanced Machine Learning Analysis. Clin EEG Neurosci. Sep. 2021;52(5):330-337.
Henderson et al., Near-infrared photonic energy penetration: can infrared phototherapy effectively reach the human brain? Neuropsychiatr Dis Treat. Aug. 21, 2015;11:2191-208.
Hipskind et al., Pulsed Transcranial Red/Near-Infrared Light Therapy Using Light-Emitting Diodes Improves Cerebral Blood Flow and Cognitive Function in Veterans with Chronic Traumatic Brain Injury: A Case Series. Photobiomodulation, Photomedicine, and Laser Surgery. 2019;37(2):77-84.
Ibrahim et al., Wireless multichannel electroencephalography in the newborn. J Neonatal Perinatal Med. 2016;9(4):341-348.
Jahan et al., Transcranial near-infrared photobiomodulation could modulate brain electrophysiological features and attentional performance in healthy young adults. Lasers Med Sci. Aug. 2019;34(6):1193-1200.
Leisman et al., Effects of Low-Level Laser Therapy in Autism Spectrum Disorder. Adv Exp Med Biol—Clinical and Experimental Biomedicine. 2018;3:111-130.
Mason et al., Nitric oxide inhibition of respiration involves both competitive (heme) and noncompetitive (copper) binding to cytochrome c oxidase. Proc Natl Acad Sci U S A. Jan. 17, 2006;103(3):708-13.
McKendrick et al., Wearable functional near infrared spectroscopy (fNIRS) and transcranial direct current stimulation (tDCS): expanding vistas for neurocognitive augmentation. Frontiers in Systems Neuroscience. Mar. 9, 2015;9(27):1-14.
Medina et al., Proceedings of the 2016 annual meeting of the Fetal Alcohol Spectrum Disorders Study Group. Alcohol. Dec. 2017;65:19-24.
MGH News and Public Affairs, Let there be light, Study led by Mass. General suggests light therapy is safe and may help patients with moderate brain injury. The Harvard Gazette, Health & Medicine. 5 pages, Sep. 23, 2020.
Mocciaro et al., Non-Invasive Transcranial Nano-Pulsed Laser Therapy Ameliorates Cognitive Function and Prevents Aberrant Migration of Neural Progenitor Cells in the Hippocampus of Rats Subjected to Traumatic Brain Injury. Journal of Neurotrauma. 2020;37:1-6.
Moinnereau et al., Classification of Auditory Stimuli from EEG Signals with a Regulated Recurrent Neural Network Reservoir. Cornell University, retrieved online at: https://arxiv.org/abs/1804.10322#. 5 pages, Apr. 27, 2018.
Roy et al., Deep learning-based electroencephalography analysis: a systematic review. J Neural Eng. 2019;16:051001, 37 pages.
Salehpour et al., Therapeutic potential of intranasal photobiomodulation therapy for neurological and neuropsychiatric disorders: a narrative review. Rev Neurosci. Apr. 28, 2020;31(3):269-286.
Salehpour et al., Transcranial near-infrared photobiomodulation attenuates memory impairment and hippocampal oxidative stress in sleep-deprived mice. Brain Res. Mar. 1, 2018;1682:36-43.
Semyachkina-Glushkovskaya et al., Photobiomodulation of lymphatic drainage and clearance: perspective strategy for augmentation of meningeal lymphatic functions. Biomed Opt Express. Jan. 10, 2020;11(2):725-734.
Shen et al., Luminous fabric devices for wearable low-level light therapy. Biomed Opt Express. Nov. 22, 2013;4(12):2925-37.
Smith et al., Automated Measurement of Pediatric Cranial Bone Thickness and Density from Clinical Computed Tomography. Conf Proc IEEE Eng Med Biol Soc. 2012;2012:4462-4465.
Tozlu et al., Machine Learning Methods Predict Individual Upper-Limb Motor Impairment Following Therapy in Chronic Stroke. Neurorehabil Neural Repair. May 2020;34(5):428-439.
Vahid et al., Applying deep learning to single-trial EEG data provides evidence for complementary theories on action control. Communications Biology. 2020;3(112):1-11.
Wilcox et al., Using near-infrared spectroscopy to assess neural activation during object processing in infants. J Biomed Opt. Jan.-Feb. 2005;10(1):11010. 9 pages.
Zolkipli-Cunningham et al., Metabolic and behavioral features of acute hyperpurinergia and the maternal immune activation mouse model of autism spectrum disorder. PLoS One. Mar. 18, 2021;16(3):e0248771, 45 pages.
International Search Report and Written Opinion for Application No. PCT/US2020/055782, dated Mar. 18, 2021, 21 pages.
Invitation to Pay Additional Fees for Application No. PCT/US2020/055782, dated Jan. 25, 2021, 12 pages.
Invitation to Pay Additional Fees for Application No. PCT/US2022/020770, dated Jun. 23, 2022, 17 pages.
Gajawelli et al., Neurocranium thickness mapping in early childhood. Sci Rep. Oct. 6, 2020;10(1): 16651, 9 pages.
Li et al., A statistical skull geometry model for children 0-3 years old. PLoS One. May 18, 20158;10(5):e0127322, 13 pages.
Zomorrodi et al., Pulsed Near Infrared Transcranial and Intranasal Photobiomodulation Significantly Modulates Neural Oscillations: a pilot exploratory study. Sci Rep. Apr. 19, 2019;9(1):6309, 11 pages.
International Search Report and Written Opinion for Application No. PCT/US2023/036721, dated May 7, 2024, 20 pages.
International Search Report and Written Opinion for Application No. PCT/US2022/020770, dated Aug. 12, 2022, 22 pages.
U.S. Appl. No. 29/72/8,109, filed Mar. 16, 2020, Des. 949,355, Issued.

(56) References Cited

OTHER PUBLICATIONS

U.S. Appl. No. 17/769,708, filed Apr. 15, 2022, 2022-0387818, Published.
U.S. Appl. No. 18/111,258, filed Feb. 17, 2023, 2023-0285772, Published.
U.S. Appl. No. 17/105,313, filed Nov. 25, 2020, U.S. Pat. No. 11,986,667, Issued.
U.S. Appl. No. 17/949,997, filed Sep. 21, 2022, 2023-0092770, Published.
U.S. Appl. No. 18/662,858, filed May 13, 2024, 2024-0293679, Published.

* cited by examiner

*Battery Discharge Curve*

Selecting manual and/or preset parameters for delivery of transcranial illumination of a patient using a system including a computing device in communication with a head wearable device having a plurality of light emitters, the system having one or more sensors to detect a characteristic of the patient at least one of before, during, and after a therapeutic session performed with the system __502__

↓

Performing transcranial illumination of the patient using selected parameter values and recording data associated with a therapeutic session including sensor data and illumination data including power distribution of the illuminating light within brain tissue of the patient as a function of time __504__

↓

Optionally, modifying one or more operating parameters of the transcranial illumination therapeutic session using detected sensor data, the one or more operating parameters including a light transmission frequency, amplitude and duration of the transmitted light and light pulse transmission frequency and pulse width emitted by each of the plurality of light emitters __506__

↓

Communicating the illumination data and the detected sensor data to a computing device to analyze the data and store the data in a medical record for the patient __508__

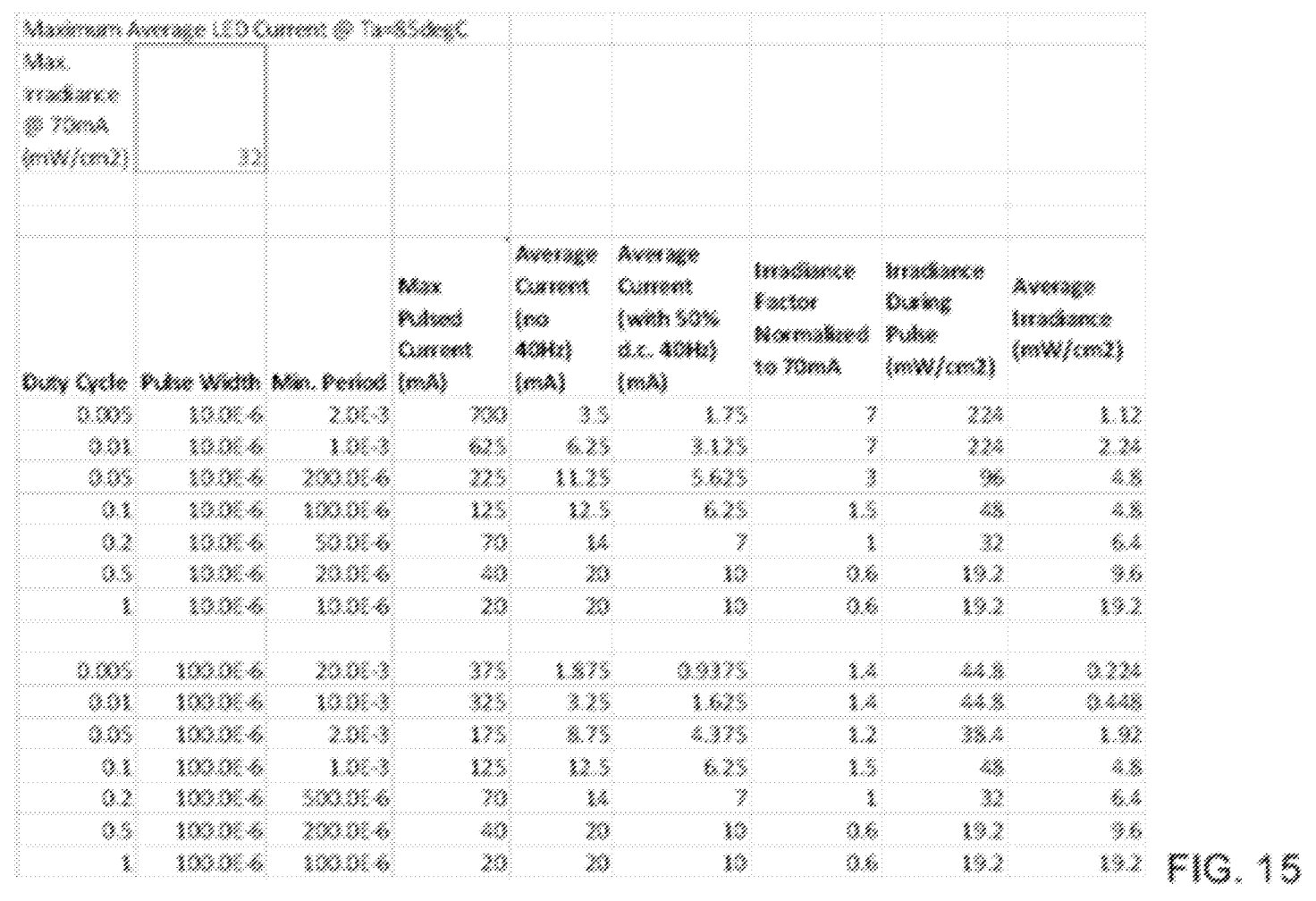

| Maximum Average LED Current @ 70mA/cm² | | | | | | | | |
|---|---|---|---|---|---|---|---|---|
| Max. Irradiance @ 70mA (mW/cm²) | Duty Cycle | Pulse Width (min. Period) | Min. Period | Max Pulsed Current (mA) | Average Current (e.g. 40Hz) (mA) | Average Current (with 50% d.c. 40Hz) (mA) | Irradiance Factor Normalized to 70mA | Irradiance During Pulse (mW/cm²) | Average Irradiance (mW/cm²) |
| 32 | 0.005 | 100.0E-6 | 20.0E-3 | 700 | 3.5 | 1.75 | 7 | 22.4 | 1.12 |
| | 0.01 | 100.0E-6 | 1.0E-3 | 635 | 6.35 | 3.125 | 7 | 22.4 | 2.24 |
| | 0.05 | 100.0E-6 | 200.0E-6 | 225 | 11.25 | 5.625 | 3 | 96 | 4.8 |
| | 0.1 | 100.0E-6 | 100.0E-6 | 125 | 12.5 | 6.25 | 1.5 | 48 | 4.8 |
| | 0.2 | 100.0E-6 | 500.0E-6 | 70 | 14 | 7 | 1 | 32 | 6.4 |
| | 0.5 | 100.0E-6 | 200.0E-6 | 40 | 20 | 10 | 0.6 | 19.2 | 9.6 |
| | 1 | 100.0E-6 | 100.0E-6 | 20 | 20 | 10 | 0.6 | 19.2 | 19.2 |
| | 0.005 | 100.0E-6 | 20.0E-3 | 375 | 1.875 | 0.9375 | 1.4 | 44.8 | 0.224 |
| | 0.01 | 100.0E-6 | 1.0E-3 | 325 | 3.25 | 1.625 | 1.4 | 44.8 | 0.448 |
| | 0.05 | 100.0E-6 | 2.0E-3 | 175 | 8.75 | 4.375 | 1.2 | 38.4 | 1.92 |
| | 0.1 | 100.0E-6 | 1.0E-3 | 125 | 12.5 | 6.25 | 1.5 | 48 | 4.8 |
| | 0.2 | 100.0E-6 | 500.0E-6 | 70 | 14 | 7 | 1 | 32 | 6.4 |
| | 0.5 | 100.0E-6 | 200.0E-6 | 40 | 20 | 10 | 0.6 | 19.2 | 9.6 |
| | 1 | 100.0E-6 | 100.0E-6 | 20 | 20 | 10 | 0.6 | 19.2 | 19.2 |

FIG. 15

HEAD WEARABLE LIGHT THERAPY DEVICE

CROSS REFERENCE TO RELATED APPLICATIONS

This application is continuation of U.S. application Ser. No. 17/769,708 filed on Apr. 15, 2022 which is a 35 U.S.C. § 371 national stage filing of International Application No. PCT/US2020/055782, filed on Oct. 15, 2020, which claims priority to U.S. Provisional Application No. 63/033,756, filed Jun. 2, 2020, U.S. Provisional Application No. 62/940,788, filed Nov. 26, 2019, and U.S. Provisional Application No. 62/915,221, filed Oct. 15, 2019, the entire contents of each of the above applications being incorporated herein by reference. This application is also related to U.S. Design application Ser. No. 29/728,109, filed Mar. 16, 2020, the entire contents of that application being incorporated herein by reference.

FIELD OF THE INVENTION

The presently disclosed subject matter relates generally to methods and devices for transcranial illumination for the therapeutic treatment of neurological conditions. Preferred embodiments can include wearable devices that communicate with mobile devices such as web enabled phones and tablets to facilitate system operation and patient data analysis. This can optionally include cross-modal brain stimulation, diagnostic modalities and, more particularly, provide methods and devices for treating children suffering from autism that can optionally utilize simultaneous audio and light stimulation.

BACKGROUND

Research indicates that in treating many neurological and psychiatric conditions, a strong combinatory effect of two separate types of treatments exists. For example, in the treatment of depression and anxiety, a combination of both medications and cognitive behavioral therapy (or dialectic behavioral therapy) produces stronger effects than either one of those modalities independently.

Furthermore, music therapy and videos games have been used to treat epilepsy patients. Some of the results indicate that listening to specific musical content in combination with pharmacological treatment reduced both the frequencies of epileptic discharges and frequencies of seizures. Similarly, combining video games with pharmacological treatment has also been shown to modulate the brain neuroplasticity and improve age-related neuronal deficits and enhanced cognitive functions in older adults. Therefore, adding two types of different treatments together has been shown to improve the outcome of the overall treatment of neurological and psychiatric conditions across various domains. Overall, when treating psychiatric or neurological disorder, combinatory effects of brain stimulation through various channels is likely to be stronger than unimodal stimulation.

For children diagnosed with Autism Spectrum Disorder ("ASD"), one of the most common challenges they face is learning language. Studies show that children with ASD struggle with acquiring syntax. As a result, they cannot parse sentences, understand speech, and/or acquire or produce new words. In particular, learning language by the age of five (being able to speak full sentences) is critical for future successful integration with neuro-typical community and independent functioning. In addition, language learning may only occur during the sensitive period (REFS), which ends between 5-7 years of age. If a child does not fully learn language during that period, subsequent learning is highly effortful and achieving fluency is unlikely. Furthermore, being able to comprehend and produce language reduces tantrums and improves behavior in individuals with ASD. Therefore, delays in speech development is one of the most critical symptoms that needs to be alleviated.

Another critical symptom that needs to be alleviated in children with ASD is anxiety. General anxiety is frequently quite debilitating in ASD children and it affects, among other things, children's ability to learn and ability to integrate socially. Children with ASD are frequently prescribed medication to reduce their anxiety, but these medications often have unintended side effects and may be not effective.

In the United States, there are over 1.5 MM children currently diagnosed with ASD, and approximately 80,000 new children are diagnosed with ASD annually. Across the world, approximately 1.5 MM-2 MM new children are annually diagnosed with ASD. Autism services cost Americans approximately $250 billion a year, which includes both medical costs (outpatient care, home care, and drugs) and non-medical costs (special education services, residential services, etc.). In addition to outright costs, there are hidden ones, such as emotional stress as well as the time required to figure out and coordinate care. Research indicates that lifelong care costs can be reduced by almost two thirds with proper early intervention.

Further research indicates that ASD is often correlated with mitochondrial dysfunction. Mitochondria in brain cells of autistic individuals does not produce enough adenosine triphosphate ("ATP"). The result of mitochondria dysfunction may be especially pronounced in the brain, since it uses 20% of all the energy generated by the human body, which may lead to neuro-developmental disorders, such as ASD. Encouraging research has shown that infrared and red light may activate a child's mitochondria, and therefore increase ATP production.

Transcranial photobiomodulation ("tPBM") of the brain with near infrared and red light has been shown to be beneficial for treating various psychiatric and neurological conditions such as anxiety, stroke and traumatic brain injury. Remarkably, autism spectrum disorder may potentially be treated therapeutically with tPBM as several scientists have recently linked the disorder to mitochondria disbalance and tPBM can potentially affect mitochondria by causing it to produce more ATP. Patients treated with tPBM will absorb near infrared light, which can potentially reduce inflammation, increase oxygen flow to the brain and increase production of ATP. However, devices and methods are needed that will enable additional treatment options for various neurological conditions.

One problem with language acquisition is that many children with ASD cannot focus on the language enough to extract syntactic features of words, to parse sentences, and/or to attend to syntactic and semantic clues of speech. Therefore, their word learning may be delayed.

The problem with anxiety is that ASD children frequently get very stressed and do not know how to calm themselves before a particular learning or social situation. As a result, they are unable to participate in regular activities (such as playdates or classes).

Accordingly, there is a need for improved methods and devices providing treatment of neurological disorders and to specifically provide therapies for the treatment of children.

SUMMARY

Preferred embodiments provide devices and methods in which a head wearable device is configured to be worn by a subject that is operated to deliver illuminating wavelengths of light with sufficient energy that are absorbed by a region of brain tissue during a therapeutic period. Transcranial delivery of illuminating light can be performed with a plurality of light emitting devices mounted to the head wearable device that can also preferably include control and processing circuitry. Therefore, providing brain stimulation with one or more of, or combinations of (i) infrared, near infrared and red light to improve operational states of the brain such as by ATP production in the brain, for example, and (ii) provide additional specific linguistic input(s) to learn syntax will improve language acquisition in ASD children. Therefore, providing brain stimulation with a combination of (i) near infrared and red light to reduce anxiety and (ii) specific meditations written for ASD children will reduce anxiety. Reduced anxiety leads to both improved language learning and better social integration. Providing an audio language program specifically designed for ASD children, may focus the attention of the child on the language, provide the child with the information about linguistic markers, and improve the child's ability to communicate. This is likely to reduce lifelong care costs for affected individuals.

Preferred embodiments can use a plurality of laser diodes or light emitting diodes (LEDs) configured to emit sufficient power through the cranium of a patient to provide a therapeutic dose during a therapeutic period. This plurality of light emitting devices can be mounted to circuit boards situated on a head wearable device. For the treatment of children the spacing between light emitters in each array mounted to the head wearable device can be selected to improve penetration depth through the cranium. As the cranium of a child increases in thickness with age, the parameters of light used to penetrate the cranium will change as a function of age. As attenuation of the illuminating light will increase with age, the frequency of light, power density and spot size of each light emitter can be selectively adjusted as a function of age. The system can automatically set the illumination conditions as a function of age of the patient. The thickness of the cranium of an individual patient can also be quantitatively measured by x-ray scan and entered into the system to set the desired illumination parameters needed to deliver the required power density to the selected region of the brain. The density of the cranium can also change as a function of age and can be quantitatively measured by x-ray bone densitometer to generate further data that can be used to control and adjust the level of radiance applied to different regions of the cranium.

Aspects of the disclosed technology include methods and devices for cross-modal stimulation brain stimulation, which may be used to treat ASD children. Consistent with the disclosed embodiments, the systems and methods of their use may include a wearable device (e.g., a bandana) that includes one or more processors, transceivers, microphones, headphones, LED lights (diodes), or power sources (e.g., batteries). One exemplary method may include positioning the wearable device on the head of a patient (an ASD child). The method may further include transmitting, by the wearable device (e.g., the LED lights), a pre-defined amount of light (e.g., red or near infrared light). The method may also include simultaneously outputting, by the headphones of the wearable device or other device that can be heard or seen by the patient, a linguistic input to the patient, for example. The linguistic input may include transparent syntactic structures that facilitate, for example, learning how to parse sentences. Also, the method may include outputting specific meditations written for ASD children, that may help ease anxiety, and thus allowing ASD children to better learn language and more easily integrate socially. In some examples, the method may further include receiving a response to the linguistic input from the patient, that the one or more processors may analyze to determine the accuracy of the response and/or to generate any follow-up linguistic inputs. Further, in some examples, the frequency and/or type of light outputted by the wearable device may be adjusted based on the response received from the patient. Also, in some examples, the wearable device may be paired to a user device (e.g., via Bluetooth®) that determines and sends the linguistic input(s) to the wearable device or other devices including one or more transducer devices, such as speakers, or display devices that can generate auditory or visual signals/images that can be heard and/or seen by the patient.

The head wearable device can comprise rigid, semi-rigid or flexible substrates on which the light emitters and circuit elements are attached. The flexible substrates can include woven fabrics or polymer fibers, molded plastics or machine printed components assembled into a band that extends around the head of the patient. Circuit boards on which electrical and optical components are mounted and interconnected can be standard rigid form or they can be flexible so as to accommodate bending around the curvature of the patient's head. As children and adults have heads in a range of different sizes, it is advantageous to have a conformable material that can adjust to different sizes. More rigid head wearable devices can use foam material to provide a conformable material in contact with the patient's head. The head wearable device can be used in conjunction with diagnostic devices and systems that can be used to select the parameters for the therapeutic use of light as described herein. A computing device such as a tablet or laptop computer can be used to control diagnostic and therapeutic operations of the head worn device and other devices used in conjunction with a therapeutic session. Such computing devices can store and manage patient data and generate electronic health or medical records for storage and further use. The computing device can be programmed with software modules such as a patient data entry module, a system operating module that can include diagnostic and therapeutic submodules, and an electronic medical records module. The system can include a networked server to enable communication with remote devices, web/internet operations and remote monitoring and control by secure communication links. The computing device can include connections to electroencephalogram (EEG) electrodes to monitor brain activity before, during or after therapeutic sessions to generate diagnostic data for the patient. The EEG electrodes can be integrated with the head wearable device and be connected either directly to a processor thereon, or alternatively, can communicate by wired or wireless connection to the external computing device such as a touchscreen operated tablet display device. Light sensors that are optically coupled to the head of the patient can be used to monitor light delivery into the cranium of the patient and/or can measure light returning from the regions of the brain that receive the illuminating light. An array of near infrared sensors can be mounted on the LED panels or circuit boards, for example, that can detect reflected light or other light signals returning from the tissue that can be used to diagnose a condition of the tissue. Diagnostic data generated by the system sensors can be used to monitor the patient during a therapeutic period and can optionally be used to control operating parameters of the system during the therapy session such as by increasing or decreasing the intensity of the light delivered through the cranium or adjusting the time period or areas of the brain being illuminated during the therapy session.

Further features of the disclosed design, and the advantages offered thereby, are explained in greater detail hereinafter with reference to specific embodiments illustrated in the accompanying drawings, wherein like elements are indicated be like reference designators.

BRIEF DESCRIPTION OF THE DRAWINGS

Reference will now be made to the accompanying drawings, which are not necessarily drawn to scale, are incorporated into and constitute a portion of this disclosure, illustrate various implementations and aspects of the disclosed technology, and, together with the description, serve to explain the principles of the disclosed technology. In the drawings:

FIG. 14 is a process flow diagram illustrating the use of EEG measurements in conjunction with transcranial illumination of a patient.

FIG. 15 illustrates a table with exemplary parameters having variable ranges between upper and lower thresholds used for transcranial illumination of a patient in accordance with preferred embodiments.

DETAILED DESCRIPTION

Some implementations of the disclosed technology will be described more fully with reference to the accompanying drawings. This disclosed technology can be embodied in many different forms, however, and should not be construed as limited to the implementations set forth herein. The components described hereinafter as making up various elements of the disclosed technology are intended to be illustrative and not restrictive. Many suitable components that would perform the same or similar functions as components described herein are intended to be embraced within the scope of the disclosed electronic devices and methods. Such other components not described herein can include, but are not limited to, for example, components developed after development of the disclosed technology.

It is also to be understood that the mention of one or more method steps does not imply that the methods steps must be performed in a particular order or preclude the presence of additional method steps or intervening method steps between the steps expressly identified.

Reference will now be made in detail to exemplary embodiments of the disclosed technology, examples of which are illustrated in the accompanying drawings and disclosed herein. Wherever convenient, the same references numbers will be used throughout the drawings to refer to the same or like parts.

Figure 1:
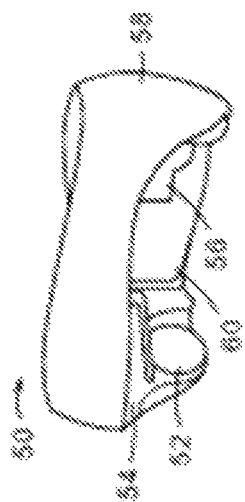
FIG. 1 is an example head wearable device, in accordance with some examples of the present disclosure.
Figure 2C:
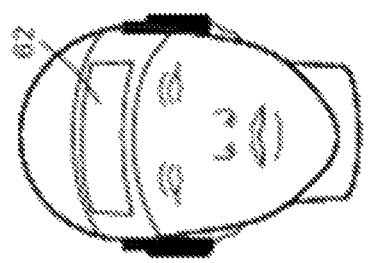
FIGS. 2A-2C show rear, side and front views of a patient with the head wearable device of FIG. 1.
Figure 2B:
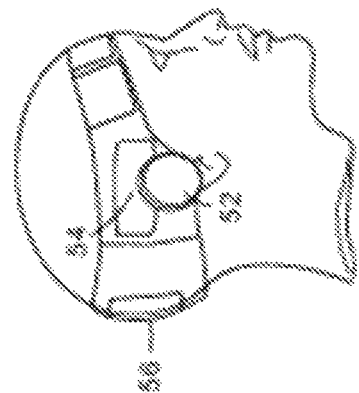
Figure 2A:
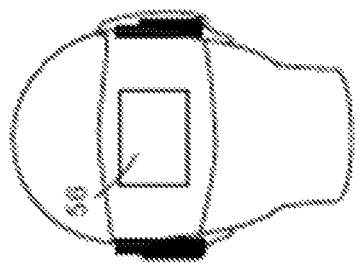

FIG. 1 shows an example wearable device 50 that may implement certain methods for cross-modal brain stimulation. As shown in FIG. 1, in some implementations the wearable device 50 may include one or more processors, transceivers, microphones, headphones 52, LED lights 54, and/or batteries, amongst other things. The wearable device 50 may be paired with a user device (e.g., smartphone, smartwatch), which may provide instructions that may determine a frequency of transmitted light, the type of light (e.g., red light or infrared light), the meditations, and/or the linguistic inputs. FIGS. 2A-2C depict rear side and front views of the head wearable device 50 positioned on the head of a patient with rear circuit board 56, side illumination panels 56, and front illumination panel 62 to provide transcranial illumination, and also earphones 52 to provide audio programming to the patient. The system can store audio files or video files that can be heard or seen by the user in conjunction with the therapeutic session for a patient.

Figure 3:
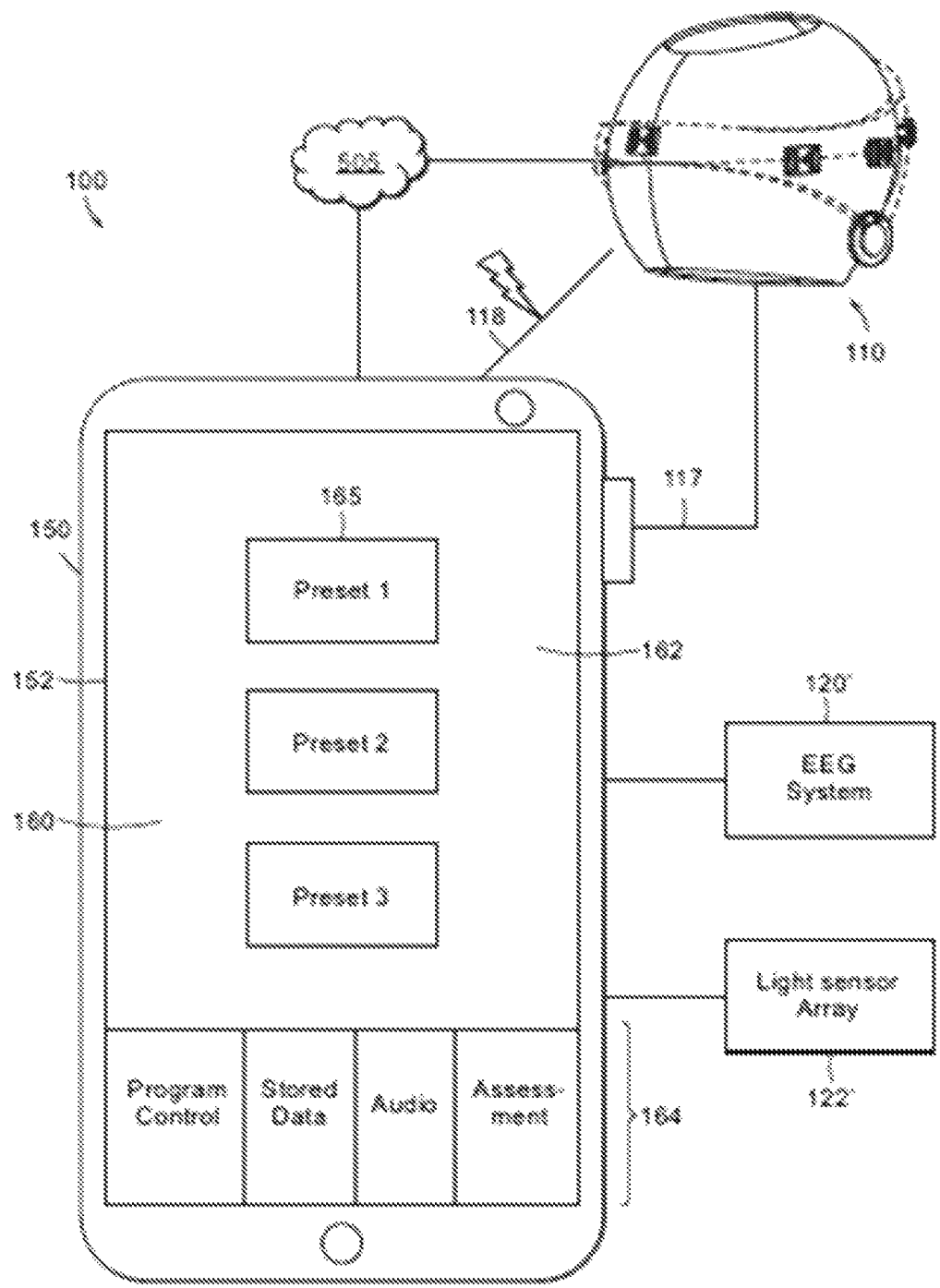
FIG. 3 illustrates use of a portable phone or tablet device connected to the head wearable device.

FIG. 3 is an illustration of a system 100 for brain stimulation in accordance with various embodiments described herein. The system 100 includes a photobiomodulation device 110 in communication with a remote computing device 150. In exemplary embodiments, the computing device 150 includes a visual display device 152 that can display a graphical user interface (GUI) 160. The GUI 160 includes an information display area 162 and user-actuatable controls 164. Optionally, the computing device 150 is also in communication with an external EEG system 120'. Optionally, the computing device 150 is also in communication with an external light sensor array 122'. An operating user can operate the computing device 150 to control operation of the photobiomodulation device 110 including activation of the functions of the photobiomodulation device 110 and mono- or bi-directional data transfer between the computing device 150 and the photobiomodulation device 110.

The operating user can change among operational modes of the computing device 150 by interacting with the user-actuatable controls 164 of the GUI 160. Examples of user-actuatable controls include controls to access program control tools, stored data and/or stored data manipulation and visualization tools, audio program tools, assessment tools, and any other suitable control modes or tools known to one of ordinary skill in the art. Upon activation of the program control mode, the GUI 160 displays program control information in the information display area 162. Likewise, activation of other modes using user-actuatable controls 164 can cause the GUI 160 to display relevant mode information in the information display area 162. The system can be programmed to perform therapeutic sessions with variable lengths of between 5 and 30 minutes, for example. The patient's use of language during the session can be recorded by microphone on the head wearable device or used separately and an analysis of language used during the session or stored for later analysis.

In the program control mode, the GUI 160 can display program controls including one or more presets 165. Activation of the preset by the operating user configures the photobiomodulation device 110 to use specific pre-set variables appropriate to light therapy for a particular class of patients or to a specific patient. For example, a specific preset 165 can correspond to a class of patient having a particular age or particular condition. In various embodiments, the pre-set variables that are configured through the preset 165 can include illumination patterns (e.g., spatial patterns, temporal patterns, or both spatial and temporal patterns), illumination wavelengths/frequencies, or illumination power levels.

In some embodiments, the photobiomodulation device 110 can transmit and/or receive data from the computing device 150. For example, the photobiomodulation device 110 can transmit data to log information about a therapy session for a patient. Such data can include, for example, illumination patterns, total length of time, time spent in different phases of a therapy program, electroencephalogram (EEG) readings, and power levels used. The data can be transmitted and logged before, during, and after a therapy session. Similar data can also be received at the computing device 150 from the external EEG system 120' or the external light sensor array 122' in embodiments that utilize these components. In the stored data manipulation and/or visualization mode, the operating user can review the data logged from these sources and received at the computing device 150. In some embodiments, the data can include information regarding activities used in conjunction with the therapy session (i.e., information related to tasks presented to the patient during the therapy session such as task identity and scoring). For example, activity data can be input by an operating user on the assessment mode screen as described in greater detail below.

In the audio system mode, the user can control audio information to be delivered to the patient through speakers 116 of the photobiomodulation device 110. Audio information can include instructions to the patient in some embodiments. In other embodiments, audio information can include audio programming for different therapeutic applications.

Figure 6:
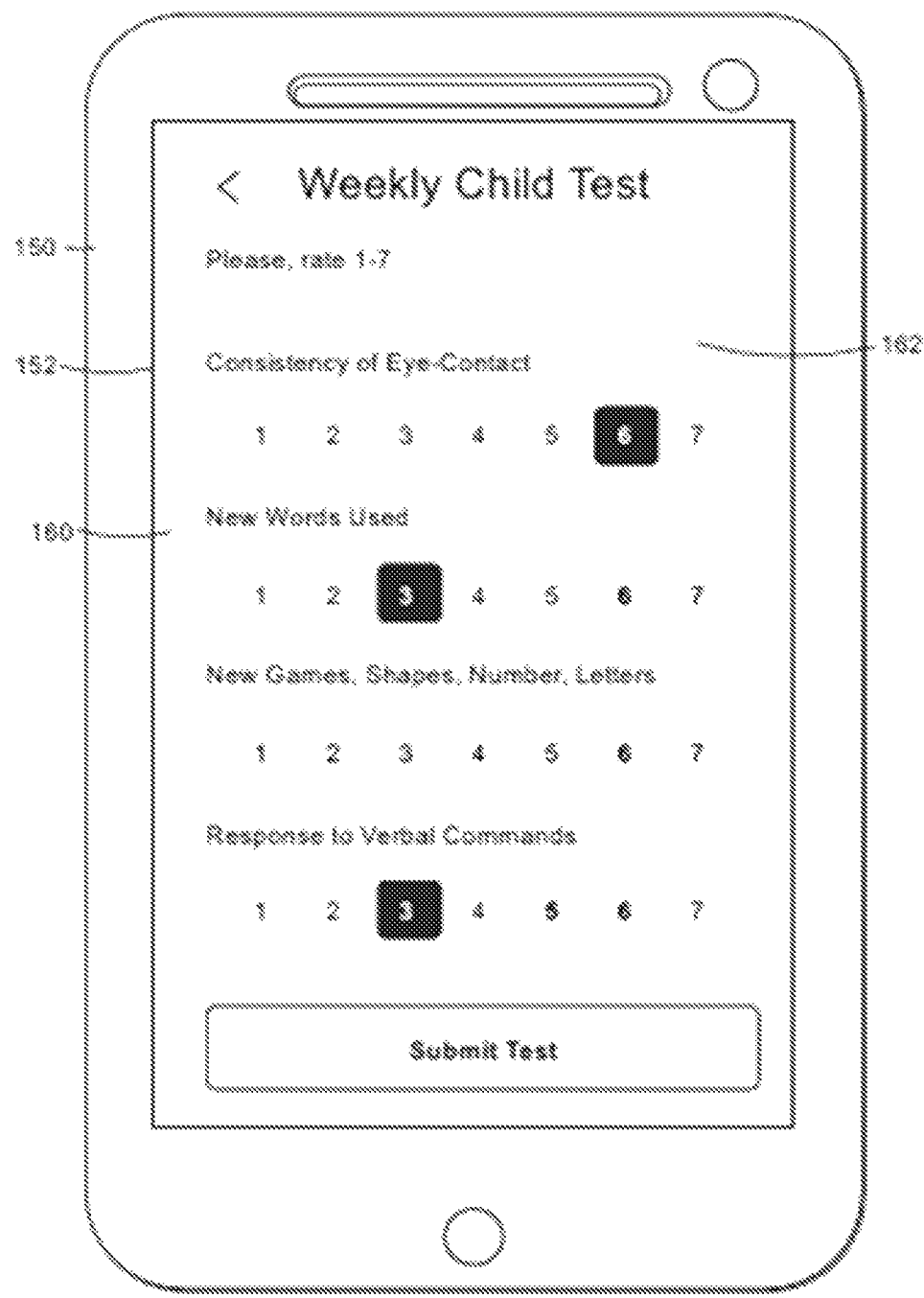
FIG. 6 illustrates a screen shot of a testing procedure used with preferred embodiments of the invention.

In the assessment mode, a user can input or review data related to patient assessment such as task identity and scoring. For example, FIG. 6 illustrates a particular assessment test displayed in the information display area 162 of the GUI 160. This assessment test, the Weekly Child Test, includes rating scales representing scoring on a variety of individual metrics geared to an overall assessment of the severity of autism in the child.

As described in greater detail below, the computing device 150 and photobiomodulation device 110 can communicate through a variety of methods. In some embodiments, a direct (i.e., wired) connection 117 can be established between the computing device 150 and the photobiomodulation device 110. In some embodiments, the computing device 150 and the photobiomodulation device 110 can communicate directly with one another through a wireless connection 118. In still further embodiments, the computing device 150 and the photobiomodulation device 110 can communication through a communications network 505.

In various embodiments, one or more portions of the communications network 505 can be an ad hoc network, a mesh network, an intranet, an extranet, a virtual private network (VPN), a local area network (LAN), a wireless LAN (WLAN), a wide area network (WAN), a wireless wide area network (WWAN), a metropolitan area network (MAN), a portion of the Internet, a portion of the Public Switched Telephone Network (PSTN), a cellular telephone network, a wireless network, a Wi-Fi network, a WiMAX network, an Internet-of-Things (IoT) network established using Bluetooth® or any other protocol, any other type of network, or a combination of two or more such networks.

In exemplary embodiments, the system 100 is configured to treat autistic patients and, in particular, juvenile autistic patients. As such, it is desirable in many embodiments to create a wireless connection between the photobiomodulation device 110 and the computing device 150 as a juvenile patient is less likely to sit still for the length of a therapy session. Wireless connection and use of a battery to power the photobiomodulation device 110 enables uninterrupted transcranial illumination for the entire length of a single therapy session and, further, enables the juvenile patient to move and engage in activities that may, or may not, be associated with the therapy.

Figure 4:
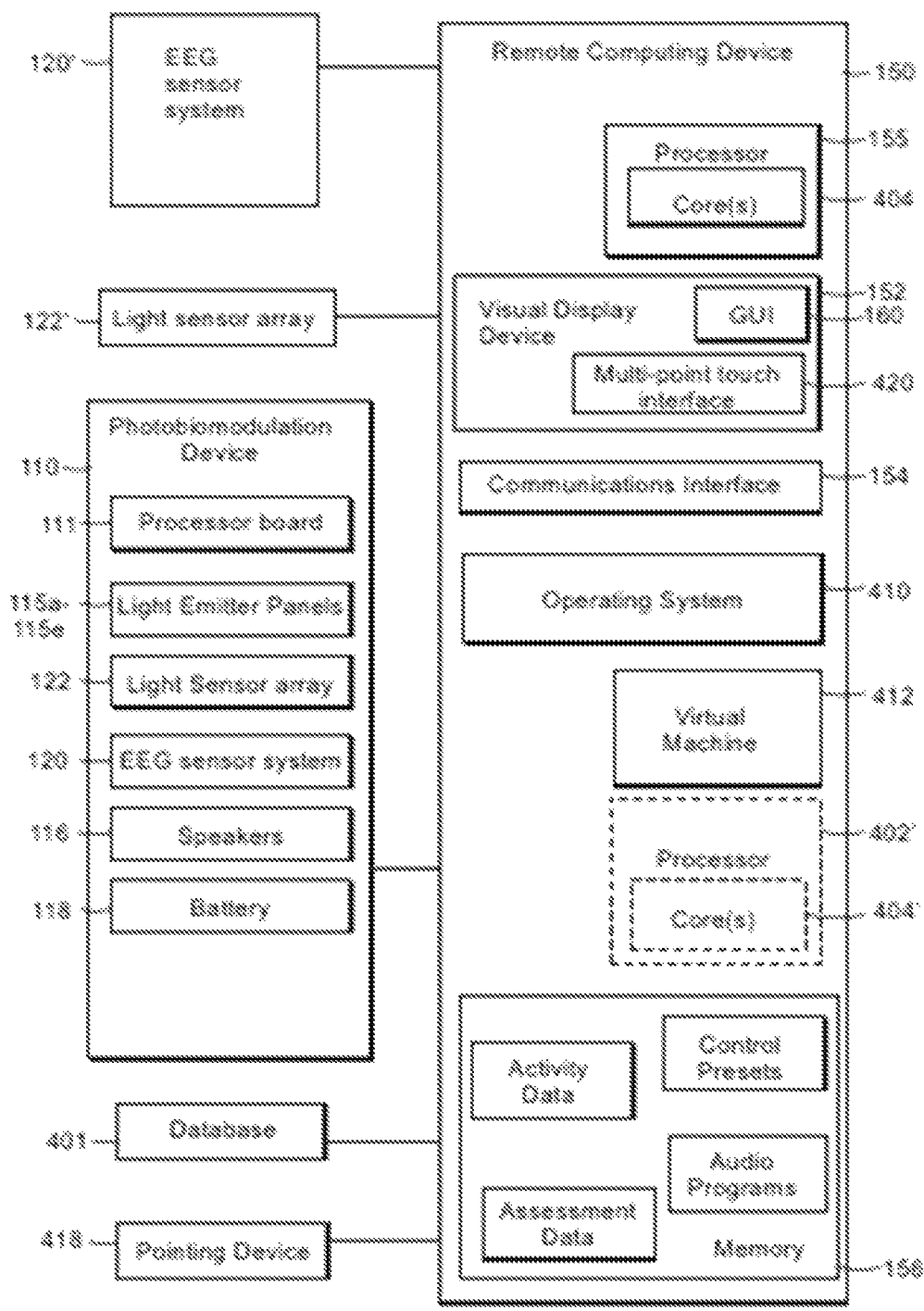
FIG. 4 schematically illustrates the operating elements of the head wearable device and control features.

FIG. 4 shows block diagrams of a remote computing device 150 and photobiomodulation device 110 suitable for use with exemplary embodiments of the present disclosure. The remote computing device 150 may be, but is not limited to, a smartphone, laptop, tablet, desktop computer, server, or network appliance. The remote computing device 150 includes one or more non-transitory computer-readable media for storing one or more computer-executable instructions or software for implementing exemplary embodiments. The non-transitory computer-readable media may include, but are not limited to, one or more types of hardware memory, non-transitory tangible media (for example, one or more magnetic storage disks, one or more optical disks, one or more flash drives, one or more solid state disks), and the like. For example, memory 156 included in the remote computing device 150 may store computer-readable and computer-executable instructions or software for implementing exemplary operations of the remote computing device 150. The remote computing device 150 also includes configurable and/or programmable processor 155 and associated core(s) 404, and optionally, one or more additional configurable and/or programmable processor(s) 402' and associated core(s) 404' (for example, in the case of computer systems having multiple processors/cores), for executing computer-readable and computer-executable instructions or software stored in the memory 156 and other programs for implementing exemplary embodiments of the present disclosure. Processor 155 and processor(s) 402' may each be a single core processor or multiple core (404 and 404') processor. Either or both of processor 155 and processor(s) 402' may be configured to execute one or more of the instructions described in connection with remote computing device 150.

Virtualization may be employed in the remote computing device 150 so that infrastructure and resources in the remote computing device 150 may be shared dynamically. A virtual machine 412 may be provided to handle a process running on multiple processors so that the process appears to be using only one computing resource rather than multiple computing resources. Multiple virtual machines may also be used with one processor.

Memory 156 may include a computer system memory or random access memory, such as DRAM, SRAM, EDO RAM, and the like. Memory 156 may include other types of memory as well, or combinations thereof.

A user may interact with the remote computing device 150 through a visual display device 152, such as a computer monitor, which may display one or more graphical user interfaces 160. In exemplary embodiments, the visual display device includes a multi-point touch interface 420 (e.g., touchscreen) that can receive tactile input from an operating user. The operating user may interact with the remote computing device 150 using the multi-point touch interface 420 or a pointing device 418.

The remote computing device 150 may also interact with one or more computer storage devices or databases 401, such as a hard-drive, CD-ROM, or other computer readable media, for storing data and computer-readable instructions and/or software that implement exemplary embodiments of the present disclosure (e.g., applications). For example, exemplary storage device 401 can include modules to execute aspects of the GUI 160 or control presets, audio programs, activity data, or assessment data. The database(s) 401 may be updated manually or automatically at any suitable time to add, delete, and/or update one or more data items in the databases. The remote computing device 150 can send data to or receive data from the database 401 including, for example, patient data, program data, or computer-executable instructions.

The remote computing device 150 can include a communications interface 154 configured to interface via one or more network devices with one or more networks, for example, Local Area Network (LAN), Wide Area Network (WAN) or the Internet through a variety of connections including, but not limited to, standard telephone lines, LAN or WAN links (for example, 802.11, T1, T3, 56 kb, X.25), broadband connections (for example, ISDN, Frame Relay, ATM), wireless connections (for example, WiFi or Bluetooth®), controller area network (CAN), or some combination of any or all of the above. In exemplary embodiments, the remote computing device 150 can include one or more antennas to facilitate wireless communication (e.g., via the network interface) between the remote computing device 150 and a network and/or between the remote computing device 150 and the photobiomodulation device 100. The communications interface 154 may include a built-in network adapter, network interface card, PCMCIA network card, card bus network adapter, wireless network adapter, USB network adapter, modem or any other device suitable for interfacing the remote computing device 150 to any type of network capable of communication and performing the operations described herein.

The remote computing device 150 may run operating system 410, such as versions of the Microsoft® Windows® operating systems, different releases of the Unix and Linux operating systems, versions of the MacOS® for Macintosh computers, embedded operating systems, real-time operating systems, open source operating systems, proprietary operating systems, or other operating system capable of running on the remote computing device 150 and performing the operations described herein. In exemplary embodiments, the operating system 410 may be run in native mode or emulated mode. In an exemplary embodiment, the operating system 410 may be run on one or more cloud machine instances.

The photobiomodulation device 110 can include a processor board 111, one or more light emitter panels 115a-115e, one or more speakers 116, and one or more batteries 118. The photobiomodulation device 110 can optionally include a light sensor array 122 and an EEG sensor system 120. Although five light emitter panels 115a-115e are described with respect to this disclosure, one or ordinary skill in the art would appreciate that a greater or fewer number of panels may be used. In an exemplary embodiment, the light emitter panels 115a-115e hare flexible. In an exemplary embodiment, the light emitter panels 115a-115e are positioned at the front, top, back, and both sides of the user's head. In embodiments wherein the photobiomodulation device 110 does not have a full cap over the user's head (i.e., a headband-style device), the top panel may be omitted.

Figure 5:
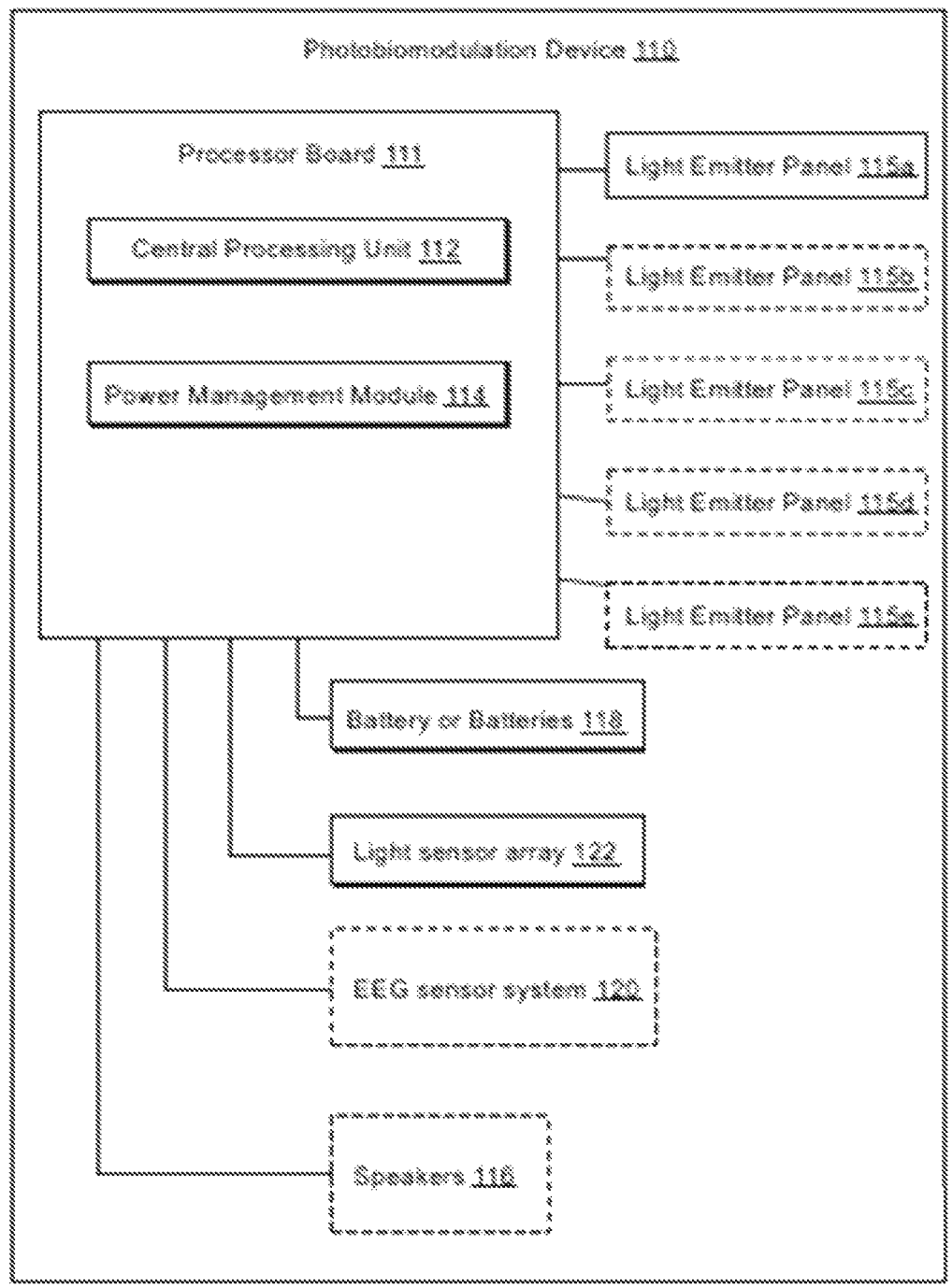
FIG. 5 schematically illustrates the components of a head wearable device in accordance with preferred embodiments.

FIG. 5 illustrates a schematic layout of the photobiomodulation device 110 of the present invention. The processor board 111 is, for example, a printed circuit board including components to control functions of the photobiomodulation device 110. The processor board 111 can include a central processing unit 112 and a power management module 114 in some embodiments.

Figure 7:
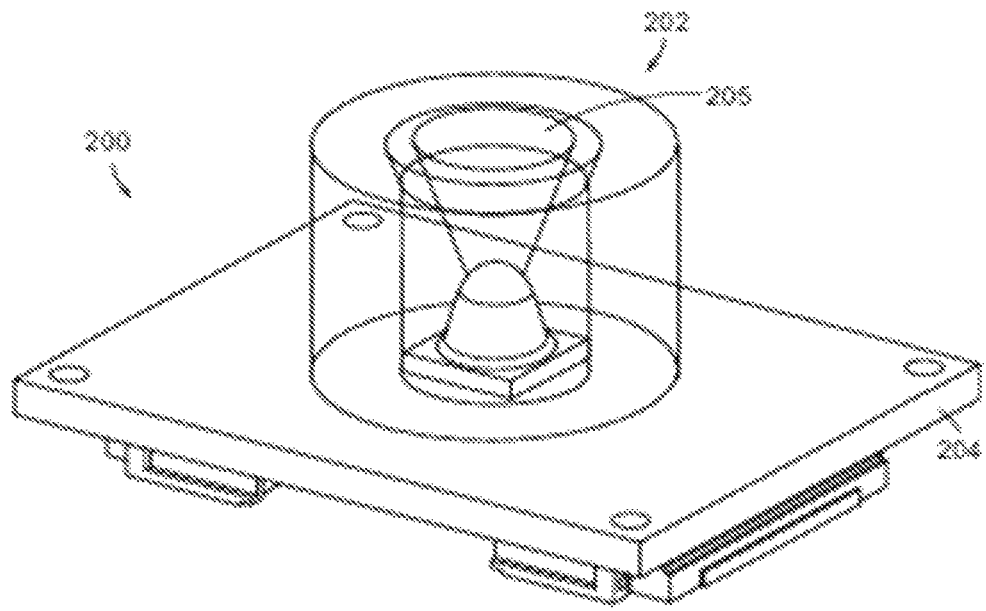
FIG. 7 illustrates a light emitter for transcranial illumination mounted on one side of a circuit board that is mounted to the head wearable device.
Figure 8:
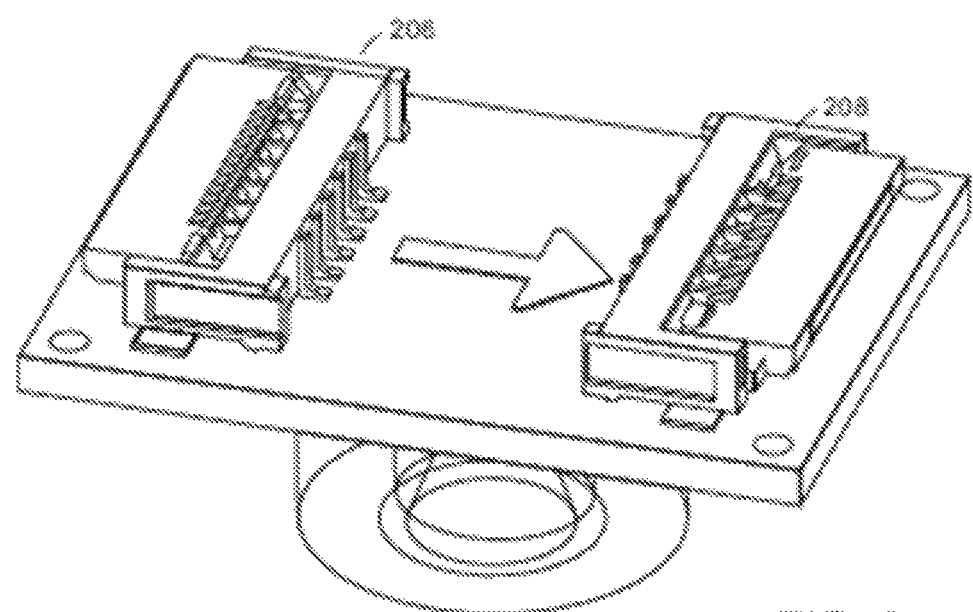
FIG. 8 illustrates a second side of the circuit board shown in FIG. 7 including connectors to the controller and power source for the head wearable device.
Figure 9:
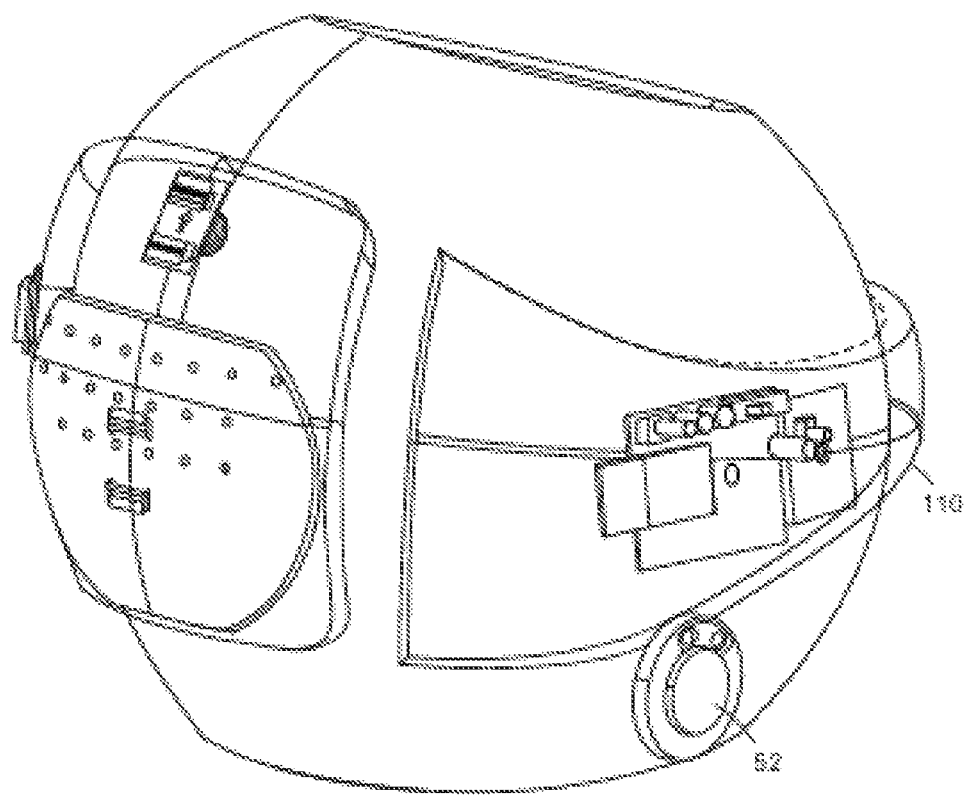
FIG. 9 illustrates a detailed view showing circuit board elements of the head wearable device of certain embodiments.
Figure 10:
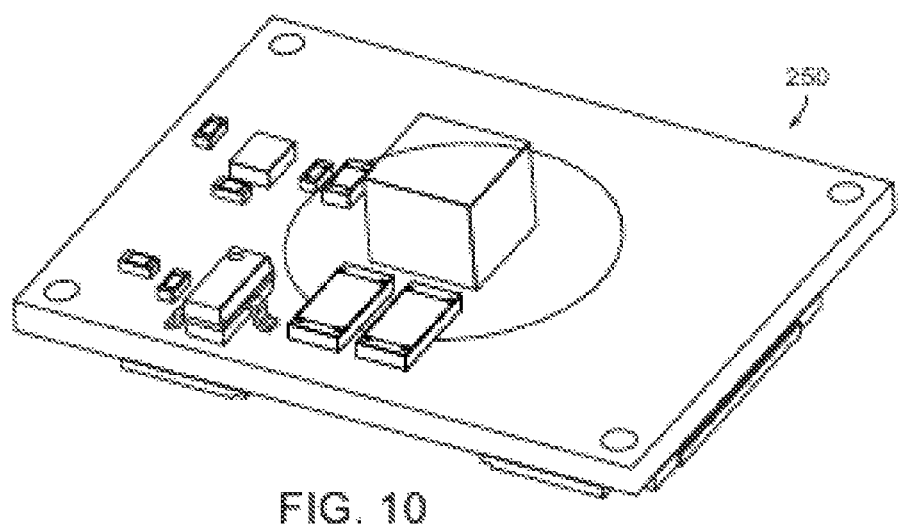
FIG. 10 shows circuitry mounted on a circuit board of the head wearable device for preferred embodiments.
Figure 11:
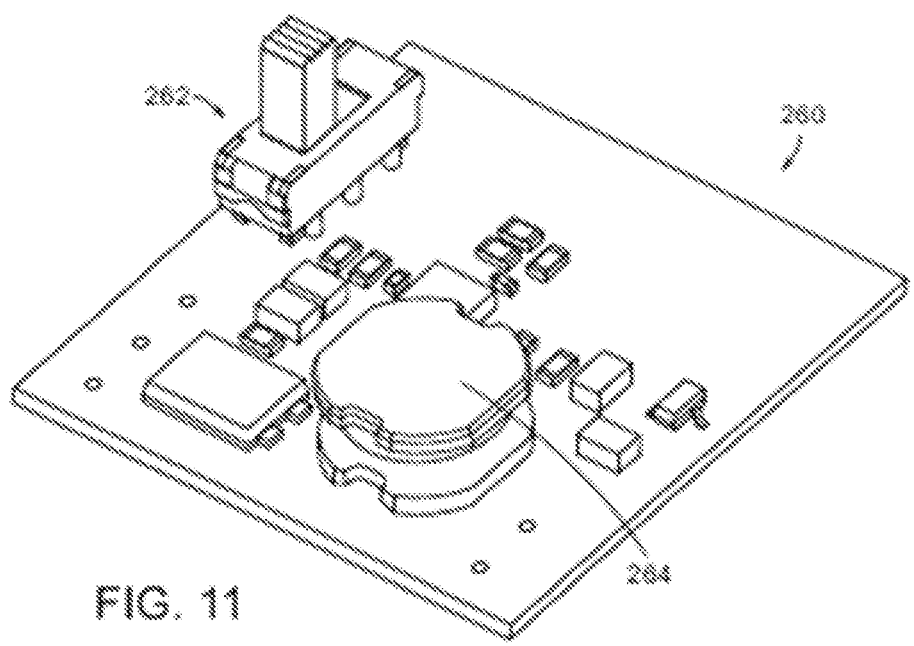
FIG. 11 shows circuitry mounted on a circuit board for control of preferred embodiments of a head wearable device.
Figure 12:
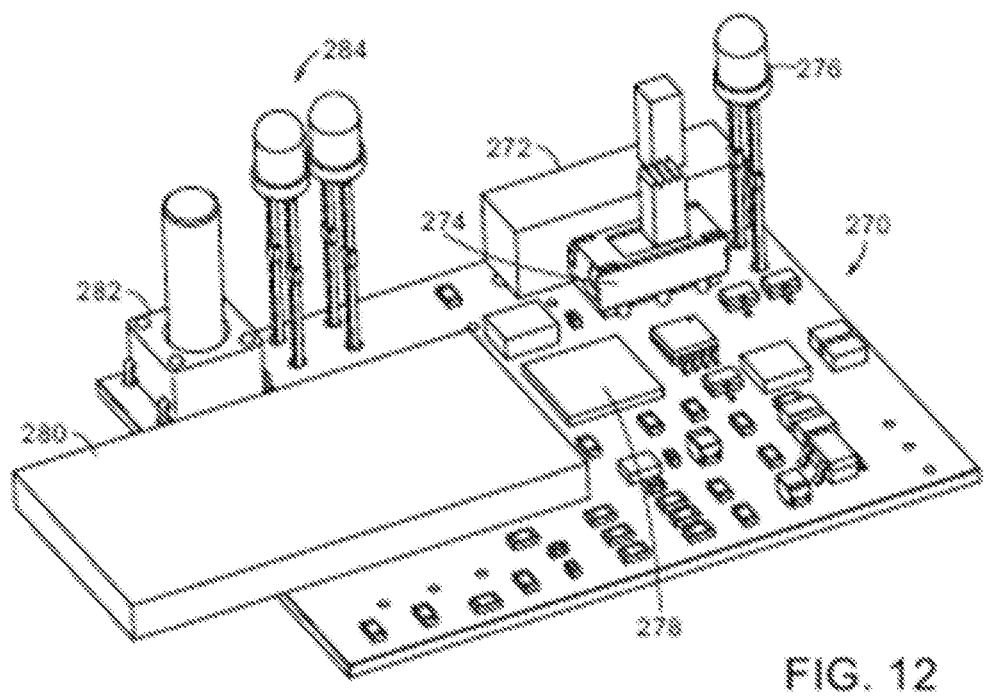
FIG. 12 shows circuitry mounted on a circuit board to control operations of the head wearable device.

The power management module 114 can monitor and control use of particular light emitter panels 115a-115e during a therapy session. In some embodiments, the power management module 114 can take action to control or provide feedback to a patient user related to whether light emitter panels 115a-115e are not used, or are only partially used, during a particular therapy session. By mitigating use of certain panels during a session, longer operation can be achieved. Moreover, different classes of patient (e.g., patients of different ages) can have different cranial thicknesses. As a result, different transmission power (and penetration) may be necessary as a function of patient age. The power management module 114 can control power output to light emitter panels to provide a therapeutically beneficial dose of illumination while still extending battery life. Shown in FIG. 7 is an LED 202 mounted on a first side of a printed circuit board 200 which can have connectors 208 for wiring to the main circuit panel 270 shown in FIG. 12. The LED 202 can have a fixed spot size 205 as it enters the cranium of the patient. Alternatively, the spot size can be reduced or increased by selected amounts to either reduce the volume of brain tissue illuminated, or increase the volume. The LED panel shown in FIG. 7 can include sensor components such as EEG electrodes and/or photodetectors configured to detect light from the illuminated tissue within the cranium. The circuit panel 270 can include a wireless transceiver to transmit and receive data from the external controller within the tablet as described herein. The circuit panel 270 can also include a wired connector to connect the system to an external power source and the tablet used to control the system. As shown in FIG. 12, two manual switches 272, 274 can be used to actuate different power levels of the system. In this specific example a first switch selects between two different levels and the second switch selects among four different settings or sublevels for a total of eight different options. These switches can also be controlled remotely from a tablet as described herein. An LED 276 is used to indicate to a user that the power is on. A further switch 282 can turn on the wireless transmitter 280, which in this implementation, is a Bluetooth transceiver. LEDs 284 can further indicate the status of the transmitter. A central microprocessor 278 is programmed to control operations of circuit board 270. The power supply board 250 and controller board 260 shown in FIGS. 10 and 11 regulate power from the one or more batteries to the controller board. The on/off power switch 262 for the head worn device can be located on board 260 which includes an inductor 264 so that the voltage delivered to the LEDs does not vary as power is drawn from the batteries. These components are mounted on the head wearable device 110 with earphones 52 which are driven by the main controller board so that the patient can hear audio files used during therapeutic sessions. Alternatively, the electronics shown and described herein can be implemented using integrated circuit components to reduce size, weight and power requirements. An electronic sensor can monitor the voltage applied to one or more LEDs so as to record the amount of optical power delivered to the patient. The electronics can be implemented as an application specific integrated circuit (ASIC) or a system on chip (SOC) design.

Autism Spectrum Disorder (ASD) is a neurodevelopmental disorder characterized by diminished social functioning, inattentiveness, and linguistic impairment. While autism is likely to be a multi-causal disorder, research indicates that individuals with ASD frequently have mitochondrial disease which results in abnormalities of energy generation from food proteins. However, mitochondria in the brain might be able to produce energy molecules from a different source, such as light.

Using the wearable device 50, certain methods of the present disclosure may perform photobiomodulation (stimulating brain with light) and linguistic training simultaneously to treat children with ASD. The wearable device 50 may include several near infrared and/or red lights to stimulate the language area of the brain. These methods associated with the wearable device 50 may include determining an area of the head to position the wearable device 50 (e.g., the temporal lobe, the prefrontal cortex, and/or the occipital lobe) to output the infrared and/or red lights. The light absorbed by the brain tissue may increase the production of ATP, which may provide the neurons more energy to communicate with each other and provide increased brain connectedness. The wearable device 50 may simultaneously receive linguistic inputs from an application of a user device that is transmitted to the user via the headphones of the wearable device 50. The linguistic inputs may help facilitate language learning. Therefore, by providing these combined mechanisms (photobiomodulation and linguistic input), for example, to children diagnosed with ASD, may significantly improve lifelong outcomes. Further, the wearable device 50 may output meditations that may help reduce anxiety of the patient user (such as an ASD child), which may allow the user to better learn language and integrate socially.

Methods for providing cross-modal brain stimulation may include determining the light frequency, location of the LED lights (e.g., areas of the brain needing increased ATP, areas of the brain most likely to respond to light treatments, and/or areas of the brain associated with language (e.g., auditory cortex, Broca area, Wernike area)), whether ATP production increased, and the overall effect of the treatments. Accordingly, based on the determined overall effect on the brain, the wearable device may be dynamically adjusted on a user-specific basis.

The wearable device 50 may be specifically tailored for children with ASD, such that it improves language skills, alleviates anxiety, and/or reduces tantrums. Further, the wearable device 50 may be used on a daily basis, in the convenience of the family's home, without a need for a specially trained therapist. Moreover, the wearable device 50 may be non-invasive, may not require a prescription, and/or may lack side effects.

Methods for using the devices of the present disclosure may further include determining the location(s) of the light emitting diodes that may be used to stimulate specific brain areas responsible for language, comprehension, energy production, and/or for self-regulation (e.g., reducing anxiety). The methods may also include determining total power, power density, pulsing, and/or frequency. The total power may be 400-600 mW (0.4-0.6 W) with 100-150 mW per each of four panels. The power for each panel may be selectively stepped down to the 50-100 mW range, or increased to the 150-200 mW range depending on the age or condition of the patient. Each of these ranges may be further incremented in 10 mW steps during a treatment session or between sessions. The spot size of the light generated by each LED or laser can optionally be controlled by adjusting the spacing between the light emission aperture of the LED or by using a movable lens for one or more LEDs on each circuit board that can be moved between adjustable positions by a MEMS actuator, for example.

Further, the wearable device 50 may be comprised of a comfortable material for prospective patients. For example, the wearable device may be comprised of plastic, fabric (e.g., cotton, polyether, rayon, etc.), and/or the like. Because ASD patients in particular are especially sensitive, the aforementioned materials may be integral in allowing ASD patients to wear it for a sufficient amount of time without being irritable. Of course, the wearable device 50 may need to be both safe and comfortable. The electric components (e.g., processors, microphones, headphones, etc.) may be sewn into the wearable device 50 and may be difficult to reach by children, for example. A cloth or fabric covering can contain the head worn frame and optoelectronic components to the extent possible without interfering with the optical coupling of the LED to the cranium. Further, the weight of the wearable device 100 may be light enough to allow it to be worn comfortably. Moreover, the wearable device 100 may require a power source (e.g., one or more replaceable batteries) that allows it to be portable.

Regarding the linguistic inputs, a patient user device (e.g., a smartphone or tablet) may include an application that 1) performs language acquisition: (e.g., develops and records a vast number of short vignettes specifically designed to make syntactic structure transparent and teaches how to parse sentences); 2) involves a system of specifically designed mediations to alleviate anxiety; and 3) involves a system of musical rewards to keep users (children) interested and engaged.

The application may disambiguate syntactic structure of a language. Present research suggests that word learning spurt occurs after the children learn basic syntax (and it occurs at the syntactic-lexicon interface). Furthermore, without syntax children may not move beyond speaking 10-15 words, which may be used for simple labeling, but not to express their needs, wants and feelings. This means that there may be no ability for proper communication without learning syntax first. In addition, syntax may be necessary to parse the acoustic wave or sound that children hear into sentences and words. Syntax may also be necessary for specific word-learning strategies (e.g., syntactic bootstrapping).

Syntactic bootstrapping is a mechanism which children use to infer meanings of verbs from the syntactic clues. For example, when a child hears "Michael cats soup" this child infers that "cats" is a transitive verb. A classic example used by a famous psycholinguist professor Leila Gleitman is the made-up verb "Derk". By putting this verb in several syntactic contexts, the meaning of the verb becomes transparent "Derk! Derk up! Derk here! Derk at me! Derk what you did!" Dr. Gleitman argued that children infer the meanings of verbs from hearing them in different syntactic contexts. In addition, Dr. Pinker argued that children also use semantic bootstrapping (contextual clues) to infer meanings of the words. Therefore, there are several mechanisms (most likely innate) available to a typical child while learning language. Overall, there is scientific consensus that typical children learn language by specifically focusing on syntactic and semantic clues of speech.

However, studies suggest that children who are on the autism spectrum cannot always extract syntactic structure and semantic contexts from the imperfect linguistic input they receive. Usual linguistic input is too messy, incomplete and confusing for them. People frequently speak in fragments of sentences, switch between topics, use incorrect words or use words in incorrect forms. Human speech may be too messy to allow for simple learning based on this type of speech alone. Neurotypical children can still extract syntactic structure from this messy input by being predisposed to pay attention to specific syntactic cues (e.g., to look for nouns and verbs in the string of speech). When children grasp syntactic structure of a language, they learn to parse sentences, and therefore, acquire more words. Several studies corroborated this hypothesis that massive word learning happens at this syntax-lexicon interface, including studies with children on the spectrum.

Many children suffering from ASD seem to be unable to move beyond simple labeling, are unable to speak in full sentences, and therefore are unable to communicate effectively. There are many reasons for this difficulty, one of them is that those children do not usually pay enough attention to speech and communication, and therefore they do not pay enough attention to syntactic clues and are not able to parse individual sentences. However, without grasping syntactic structure of the language, word learning beyond simple labeling becomes impossible, specifically, acquisition of verbs may become impossible. Timely acquisition of verbs (not just nouns to label objects around them) may be critical for ASD children, as research shows that the best predictor of future integration with the neuro-typical community (and normal functioning) is speaking full sentences by 5 years of age. Therefore, specifically, the problem is that children with ASD are not focused on the language enough to extract syntactic features of words, to parse sentences and to attend to syntactic and semantic clues of speech. Therefore, their word learning is delayed.

Accordingly, the aforementioned application may calibrate the imperfect linguistic input for ASD children, thus, making syntactic structure as transparent as possible. For example, the child will hear a noun: "dog", then she will hear "1 dog, 2 dogs, 3 dogs, 4 dogs, 5 dogs", then she will hear "my dog is brown", "my brown dog is cute", "my brown dog is small". "I have a small, cute, brown dog", "my dog barks," "dogs bark" "dogs chase cats", "dogs eat meat", "I have a dog." and so on. By putting the same word in different syntactic contexts over and over again we will flood the child with the information about linguistic markers (syntactic roles in the sentences, countable, noun, animate/inanimate and so on).

Figure 13A:
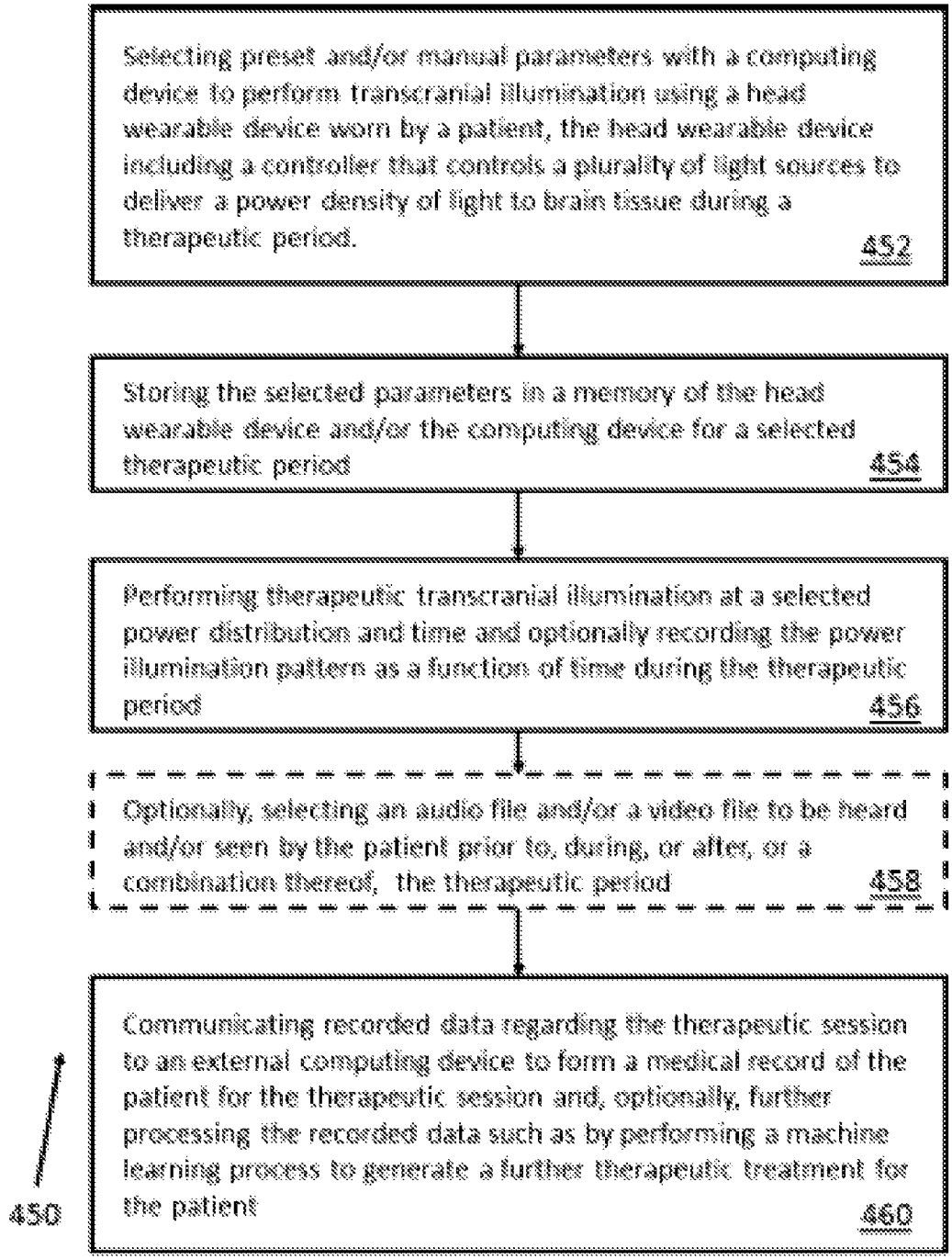
FIG. 13A is a process flow diagram in accordance with preferred methods of operating the head wearable device and control system.

Therefore, the application may "wake up" (activate) language learning and make a child pay attention to the syntactic cues of the linguistic input. Further, the application may be refined by observing the behavior of the users and recording their improvements. A method for treatment 450 is described in connection with the process flow diagram of FIG. 13A wherein preset or manually entered parameters 452 can be entered by touch actuation on the tablet touchscreen so that the system controller can actuate the illumination sequence. These parameters are stored 454 in memory. The software for the system then executes stored instructions based on the selected parameters to provide transcranial illumination 456 for the therapeutic period. The system can utilize optional audio or video files 458 in conjunction with the therapy session. The system than communicates the recorded data 460 for the therapeutic session for storage in the electronic medical record of the patient. The data can be used for further analysis such as by application of a machine learning program to provide training data.

The following describes an example of a battery powered system as previously described herein where one or two 9 volt batteries are inserted into battery holders in the side and rear views showing the LED case design shown in the figures.

If the LED is uncased, a small tube can be used to ensure that it remains centered and held securely in place. This tube can fit through a hole in the foam band for proper location and is ⅜" outside diameter. The PCB serves as a backing on the foam and allows clearance for the connecting cable. The same type of construction can be applied to the electronics mounted area, the battery, and the speakers. Sensors used to measure characteristics of the patient during use, such as EEG electrodes, photodetectors and/or temperature sensors can be mounted to the circuit boards carrying the LEDs or laser diodes as described generally herein. Detected electrical signals from the sensors can be routed to the controller board and stored in local memory and can also be transmitted via wireless transmission to the external tablet device so that a user or clinician can monitor the therapeutic session and control changes to the operating parameters of the system during use.

The electronics can comprise three or more separate PCB configurations with the LED PCB having (6) variations for the associated positions on the head. There can be two LED PCB boards on each side (front and rear) with at least one illuminating the temporal lobe on each side and at least one board centered for illuminating the frontal lobe. One or two boards can conform to one or both of the parietal lobe and the occipital lobe.

The system is fitted on the head of a patient and radiates energy via IR LEDs at 40 Hz into the patient's head, for example. The IR LEDs are split into six boards with each containing one IR LED. The LED utilized for preferred embodiments can be the SST-05-IR-B40-K850.

The LED boards can illuminate during the on-time of the 40 Hz signal. The duty cycle of the 40 Hz signal will be equal to the power setting. For example, a power setting of 25% will require a 25% duty cycle for the 40 Hz.

One or more 9V batteries can be the system's source of power. A buck converter reduces the 9V from the battery to 2.5V for the LEDs. One or more batteries of different voltages can be employed particularly where different batteries can be used for the light emitters and powering the circuitry.

In this section, note the calculation of the LED's absolute maximum optical flux output assuming that they are the only components powered by a single 9V battery.

Table 1 shows the current limits of important components. These current limits cannot be violated without the risk of permanent damage to the component.

| Device Specification | Current Limit (A) |
|---|---|
| Absolute Maximum Battery Discharge | 1.0 |
| Absolute Maximum Buck Converter Current Output | 2.5 |
| Absolute Maximum IR LED Current | 1.0 |

Conservation of energy dictates that the current sourced by the buck converter will not be the same as the current sourced by the battery. Equation 1 calculates the current drawn from the battery ($I_{BATT}$).

$$I_{BATT} = \frac{V_{LED\_PWR} \times I_{LED\_PWR}}{\eta \times V_{BATT}}$$

where $V_{LED\_PWR}$ is the LED supply voltage (2.5 V), $I_{LED\_PWR}$ is the buck converter output current, $\eta$ is the efficiency (minimum of 0.85), and $V_{BATT}$ is the battery voltage.

The efficiency of the buck converter changes over the output current range. The minimum efficiency is 0.85 at the maximum current of 2.5 A.

Note that the battery voltage is inversely proportional to the battery draw. For a fixed load, the battery will draw more current as the battery discharges. Therefore, a minimum battery voltage must be specified and observed by the system microcontroller to avoid exceeding the battery's maximum discharge current. Table 2 demonstrates how battery current draw increases as the battery discharges. Each battery draw value is calculated with Equation 1 with the following values: $\eta=0.85$, $V_{LED\_PWR}=2.5V$, $I_{LED\_PWR}=2.5$ A, and the battery voltage for $V_{BATT}$.

| Scenario | Battery Draw (mA) |
|---|---|
| Fully Charged Battery at 9 V | 816 |
| Intermediate Charge at 7.5 V | 980 |
| Absolute Minimum Battery Voltage, 7.35 V | 1000 |

Use Equation 2 to calculate the absolute minimum battery voltage, $V_{B\_AM}$. Use the same values as before, but let $I_{B\_MAX}=1$. Battery current draw reaches 1.0 A when the battery voltage discharges to 7.35V, therefore the LEDs must be turned off to avoid exceeding the L522 battery maximum discharge specification of 1.0 A. The buck converter supplying 2.5 A at 2.5V with a battery voltage below 7.35V risks permanent damage to the battery.

Absolute Minimum Battery Current Draw $$V_{B\_AM} = \frac{V_{LED\_PWR} \times I_{LED\_PWR}}{\eta \times I_{B\_MAX}}. \qquad \text{Equation 2}$$

Figure 13B:
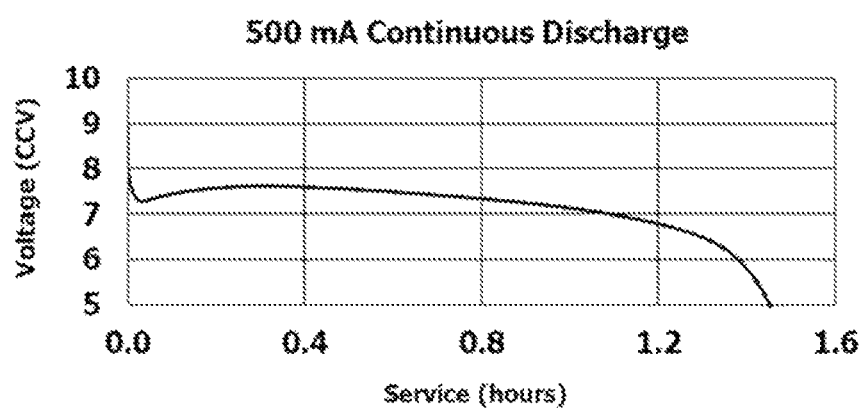
FIG. 13B depicts a diagram of a battery discharge curve.

The absolute minimum battery voltage also affects battery life. FIG. 13B illustrates a discharge curve for the (Energizer L522) battery and it demonstrates that a lower absolute minimum battery voltage prolongs battery life. With a 7.35V absolute minimum battery voltage, the LEDs can be safely powered for approximately 24 minutes (if the battery was drawing 500 mA instead of 1.0 A). Thus, a lower absolute minimum battery voltage is beneficial.

The 2.5 A sourced by the buck converter must be shared amongst six boards (LED). Thus 2.5 A/6=416 mA from the buck converter per LED.

Figure 13C:
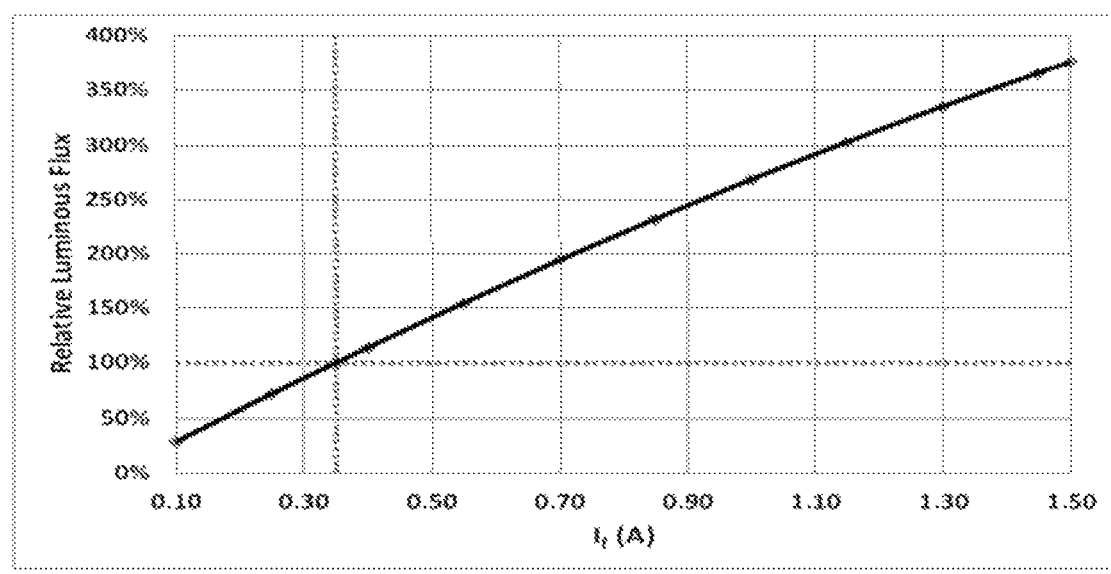
FIG. 13C depicts a diagram of relative output flux vs. forward current.

FIG. 13C illustrates the manufacturer's graph of optical flux normalized at 350 mA. The manufacturer datasheet states that the optical flux at 350 mA ranges between 265 mW and 295 mW. At 416 mA, the optical flux is approximately 110% the optical flux at 350 mA. Using the worst-case flux output of 265 mA, the optical flux at 416 mA is 265 mW×1.1=291.5 mW or approximately 292 mW.

The duty cycle of the 40 Hz will attenuate the optical flux. Equation 3 shows how to calculate the average flux for a single pulsed LED. $E_{e\_pulse}$ is the optical flux during the pulse and $D_{40\_HZ}$ is the 40 Hz duty cycle. The range of $D_{40\_HZ}$ is a number between 0 and 1 inclusive.

Average irradiance for a single LED $$E_{e\_average} = D_{40HZ} \times E_{e\_pulse}. \qquad \text{Equation 3}$$

As an example, Table 3 lists the optical flux for each power setting.

TABLE 3

Power Setting at Maximum System Power.

| Power Setting | Optical Flux Output (mW) |
|---|---|
| 2% | 5.84 |
| 4% | 11.68 |
| 6% | 17.52 |
| 8% | 23.36 |
| 16% | 46.72 |
| 25% | 73 |
| 50% | 146 |
| 100% | 292 |

The output optical flux decreases with temperature and must be de-rated accordingly. Sources of heat to take into account are the LEDs' self-heating and the heat from the patient's head. For the purposes of this analysis, assume the patient's head is at body temperature, 37° C.

TABLE 4

Temperature Related Coefficients

| Parameter | Value |
|---|---|
| Temperature Coefficient of Radiometric Power | −0.3%/° C. |
| Electrical Thermal Resistance | 9.2° C./W |

Table 4 above lists two thermal coefficients. The thermal resistance of the LED can be understood as for every watt consumed by the LED, its temperature will rise by 9.2° C. The third graph below shows normalized V-I characteristics of the LED relative to 350 mA at 2V (at 350 mA, forward voltage ranges between 1.2V and 2.0V, but here we continue to use worst-case value of 2.0V).

Figure 13D:
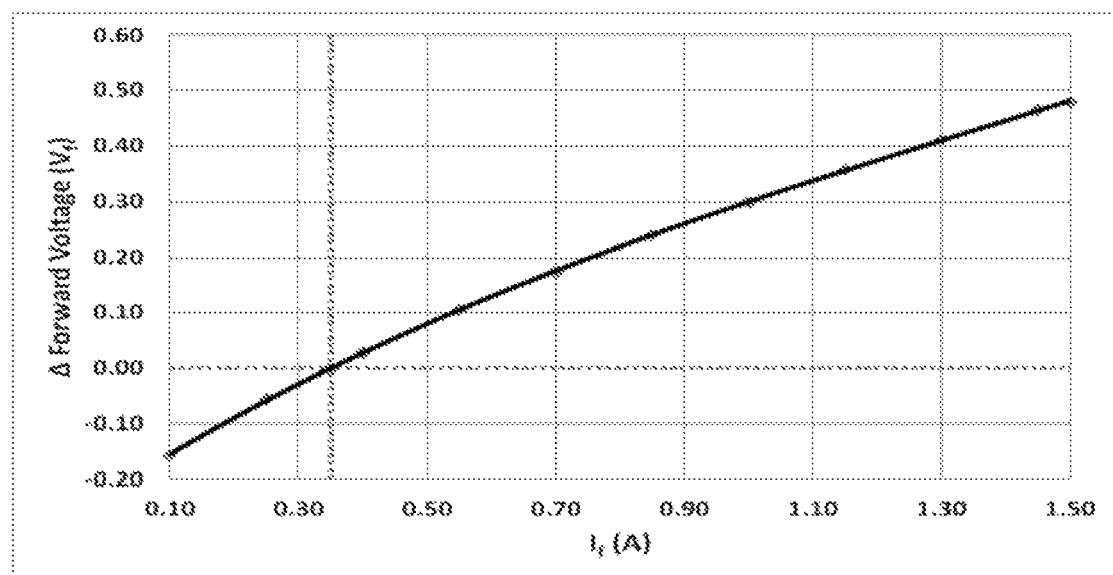
FIG. 13D depicts a diagram of relative voltage vs. forward current.

At 416 mA (the maximum current available per LED), FIG. 13D illustrates that the forward voltage is approximately 2V+0.04V=2.04V. Using Equation 4, the temperature rise due to self-heating is 7.8° C. at a 100% 40 Hz duty cycle.

Temperature Rise due to Self-Heating $$T_{\Delta_{LED}} = V_f \times I_f \times D_{40HZ} \times 9.2.$$ Equation 4

Figure 13E:
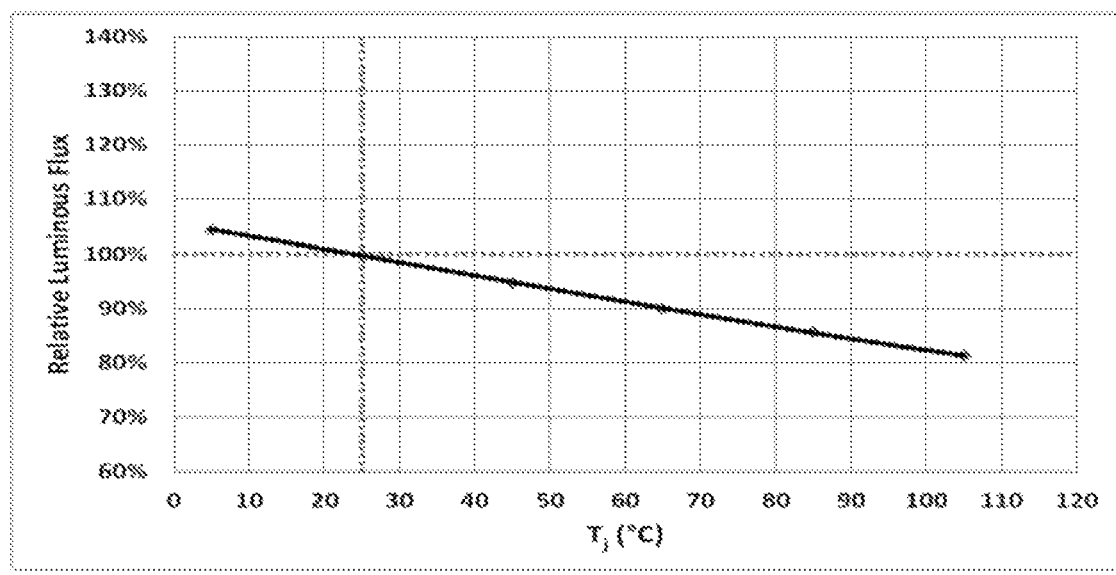
FIG. 13E depicts a diagram of relative output flux vs. temperature.

The LED can rise to a temperature of $T_{LED}$=37° C.+7.8° C.=44.8° C. The optical flux vs temperature graph depicted in FIG. 13E is normalized to 25° C. Using the temperature coefficient of radiant power from Table 4 and Equation 5, the change in radiant power due to temperature is −5.94%. Therefore, de-rating the worst-case optical flux of 292 mW derived above by 5.94% yields approximately 275 mW.

Change in Output Flux due to Temperature $$PO_{\Delta\%} = (T_{LED} - 25° C.) \times (-0.3\%/° C.).$$ Equation 5

Note that the system also provides a temperature coefficient for forward voltage. Forward voltage decreases with temperature rise. For a worst-case analysis, the decrease in forward voltage due to temperature can be ignored.

An optical flux of 275 mW is the minimum absolute maximum that can be achieved if the buck converter and the battery are pushed to their limits assuming that the battery is only supplying power to the LEDs.

Since the battery may also be powering the digital logic which includes the microcontroller, the Bluetooth module or other wireless connection, etc. the LEDs cannot draw the 1.0 A maximum from the battery.

The steps below are an effort to summarize the approach described above.
1. Start by selecting the target current for a single LED, $I_f$.
2. The current sourced by the buck converter will be $I_{LED\_PWR}$=6×$I_f$. If $I_{LED\_PWR}$ exceeds 2.5 A, you must decrease $I_f$.
3. Use Equation 2 to calculate the minimum safe battery voltage to ensure desired battery life and safe operating conditions. For efficiency, either use the worst-case value of 0.85 or select the closest efficiency for your value of $I_{LED\_PWR}$ from Table 5.

TABLE 5

| Buck Converter Efficiency for Different Output Currents | |
|---|---|
| Buck Converter Output, $I_{LED\_PWR}$ (A) | Efficiency, η |
| 2.5 | 0.85 |
| 2.0 | 0.871 |
| 1.5 | 0.89 |

TABLE 5-continued

| Buck Converter Efficiency for Different Output Currents | |
|---|---|
| Buck Converter Output, $I_{LED\_PWR}$ (A) | Efficiency, η |
| 1.0 | 0.91 |
| 0.5 | 0.926 |
| 0.25 | 0.91 |
| 0.125 | 0.88 |

4. Use graph to approximate the optical flux output at $I_f$.
   a. Note: Graph is normalized to optical flux of 265 mW at 350 mA.
5. Use graph to approximate the forward voltage at $I_f$.
   a. Note: Graph is normalized to 2.0V forward voltage at 350 mA.
6. Calculate the self-heating temperature rise, $T_{\Delta\_LED}$, using Equation 4. Use $D_{40\ Hz}$=1 for 100% 40 Hz duty cycle as the worst-case temperature rise.
7. De-rate the optical flux for a $T_{\Delta\_LED}$ rise over ambient temperature. Use 37° C. for ambient temperature. This de-rated optical flux is the maximum flux output for a single LED.

Table 6 gives examples of target LED current and the resulting system specification. Allow a 100 mA margin on the battery draw for supply logic. Values calculated in Table 6 assume worst-case efficiency of 0.85.

TABLE 6

| LED Current Target Examples. | | | | | |
|---|---|---|---|---|---|
| Target LED Current (mA) | Absolute Minimum Battery Voltage (V) | Battery Draw at 6.5 V (mA) | LED Temperature Rise (° C.) | Flux Output per LED (mW) | Flux Output per LED (temperature adjusted) (mW) |
| 100 | 1.765 | 271 | 1.7 | 57 | 55 |
| 200 | 3.529 | 543 | 3.5 | 133 | 127 |
| 300 | 5.294 | 814 | 5.4 | 207 | 196 |
| 339 | 5.982 | 900 | 6.2 | 236 | 223 |

The maximum target LED current is 339 mA resulting in a temperature adjusted flux output of 223 mW. Table 7 demonstrates how the 40 Hz duty cycle attenuates the LED output flux.

TABLE 7

| Power Settings for Realistically Maximizing Flux Output | |
|---|---|
| Power Setting | Optical Flux Output (mW) |
| 2% | 4.46 |
| 4% | 8.92 |
| 6% | 13.4 |
| 8% | 17.8 |
| 16% | 35.7 |
| 25% | 55.8 |
| 50% | 111.5 |
| 100% | 223 |

EEG can be used to augment the use of TPBM to reduce symptoms of autism, for example, and this procedure is described in further detail below.

The head wearable device reduces symptoms of autism by applying tPBM to stabilize functional brain connectivity, while using EEG data as a measure of the efficacy of tPBM and as a guide for continuous applications. The head wearable device can include EEG electrodes situated on one or more of the light emitter printed circuit boards as described herein. Between one and six EEG electrodes can be mounted on one or more of the light emitter panels so that they are interleaved between the light emitters or surround them so as to detect brain wave signals occurring during illumination.

Figure 13F:
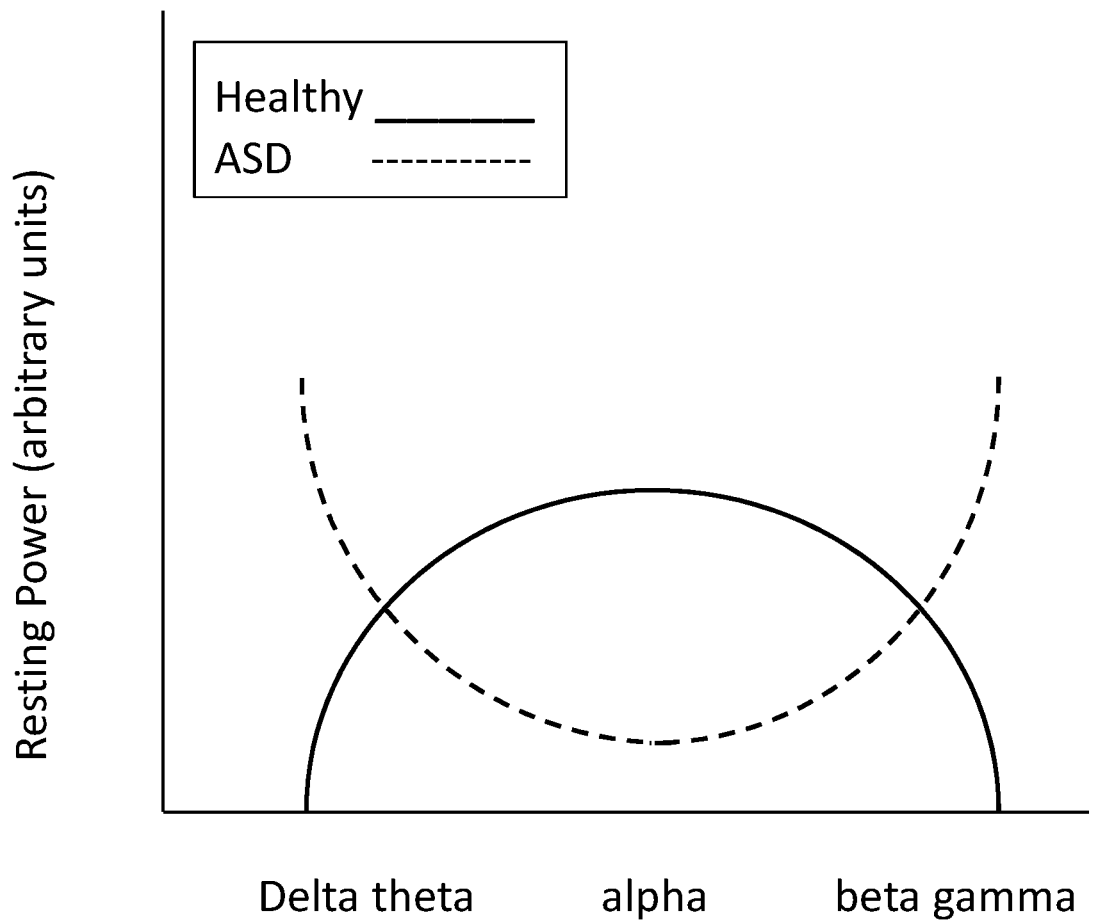
FIG. 13F depicts a battery discharge curve.

Autism (ASD) is a life-long disorder characterized by repetitive behaviors and deficiencies in verbal and non-verbal communication. Resent research identified early biomarkers of autism, including abnormalities in EEG of ASD infants, toddlers and children as compared to typical children. For example, children diagnosed with ASD present with significantly more epileptiforms (even, when they do not develop seizures), some researchers report as many as 30% of ASD children present with epileptiforms (e.g., Spence and Schneider, Pediatric Research 65, 599-606 (2009). A recent longitudinal study (from 3 to 36 months) detected abnormal developmental trajectory in delta and gamma frequencies, which allow distinguishing children with ASD diagnosis from others (Gabard-Durnam et al 2019). Short-range hyper-connectivity is also reported in ASD children. For example, Orekhova et al (2014). showed that alpha range hyper-connectivity in the frontal area at 14 months (and that it correlates with repetitive behaviors at 3 years old). Wang et al (2013), has indicated that individuals with ASD present with abnormal distribution of various brain waves. Specifically, the researchers argued that individuals with ASD show an excess power displayed in low-frequency (delta, theta) and high-frequency (beta, gamma) bands, and reduced relative and absolute power in middle-range (alpha) frequencies across many brain regions including the frontal, occipital, parietal, and temporal cortex. This pattern indicates a U-shaped profile of electrophysiological power alterations in ASD in which the extremities of the power spectrum are abnormally increased, while power in the middle frequencies is reduced. See FIG. 13F.

Duffy & Als (2019) argued, based on EEG data, that ASD is not a spectrum but rather a "cluster" disorder (as they identified two separate clusters of ASD population) and Bosl et al Scientific Reports 8, 6828 (2018) used non-linear analyses of infant EEG data to predict autism for babies as young as 3 months. Further details concerning the application of computational methods of Bosl can be found in US Patent publication 2013/0178731 filed on Mar. 25, 2013 with application Ser. No. 13/816,645, from PCT/US2011/047561 filed on Aug. 12, 2011, the entire contents of which is incorporated herein by reference. This application describes the application of machine learning and computational techniques including the use of training data stored over time for numerous patients and conditions that can be used to train the a machine learning system for use with the methods and devices described herein. A neural network can be used for example to tune the parameters employed for transcranial illumination of a child at a certain age range undergoing treatment for autism. An array of 32 or 64 EEG channels can be used with electrodes distributed around the cranium of the child. Overall, the consensus is that ASD is a functional disconnectivity disorder, which has electrophysiological markers, which can be detected through an EEG system. Dickinson et al (2017) showed that at a group level, peak alpha frequency was decreased in ASD compared to TD children.

Transcranial photobiomodulation as described herein is used to treat many neurological conditions (TBI, Alzheimer, Depression, Anxiety), and is uniquely beneficial to autism, as it increases functional connectivity AND affects brain oscillations (Zombordi, et al. 2019; Wang et al 2018). Specifically, Zomorrodi et al Scientific Reports 9 (1) 6309 (2019) showed that applying tPBM (LED-based device) to Default Mode Network increases a power of alpha, beta and gamma, while reduces the power of delta and theta (at resting state). Wang et al (2018) also showed significant increases in alpha and beta bands. Finally, Pruitt et all (2019) showed that tPBM increases cerebral metabolism of human brain (increasing ATP production).

Thus, preferred embodiments use a system that correlates continuously collected EEG data with observable symptoms (as reported by the parents) and use EEG to guide application of LED based tPBM. The symptoms provided by parents can provide ranked data can be used to formulate the parameters for a therapy session.

LED based tPBM can be applied to Default Mode Network (avoiding central midline areas) as well as Occipital lobe, and Broca area (left parietal lobe) as well as Wernike area (left temporal lobe).

Stimulating DMN (and simultaneous stimulation of frontal lobe with occipital lobe) increases long-range coherence. Stimulating language producing areas (e.g., Broca and Wernike areas with DMN) has been shown to facilitate language production in aphasic stroke patients (Naeser, 2014).

The device will:
1. Analyze initial EEG data for epileptiforms, long-range coherence and hemispheric dominance.
2. Correlate EEG data with observed symptoms.
3. Based on the observed symptoms and the EEG data, the head wearable device can apply tPBM. For example, for children with severe repetitive behaviors and strong delta and theta power in the prefrontal cortex, the device stimulates prefrontal cortex to increase power within alpha and beta frequency band (and decrease power of delta and theta bands). For children who struggle with language, the device can stimulate DMN and Broca and Wernike areas. For children with various and severe symptoms, the device can stimulate all identified targeted areas (DMN, Broca, Wernike, occipital lobes).
4. The device can adjust power gradually and increasing it until the minimal change in brain oscillation is detected. This thresholding avoids applying too much power to a developing brain. The device operates at the lowest power that achieves the desired oscillation.
5. As the symptoms improve and the measured EEG signal stabilizes, the power level of the device can be gradually reduced. This system can be automated to control each therapy session.
6. Machine learning algorithms analyze EEG data and behavioral data, and the power alterations provided by the algorithm in the form of guidance to parents (and therapists), as well as indicate further improvements in the therapy being given to the patient.
7. As the symptoms sufficiently improve (expected improvement is within 8 weeks based on Leisman et al 2018), the device controls a break from tPBM and collect only EEG and behavioral symptoms to monitor for possible regression.
8. If any regress is detected, the device can instruct that tPBM is gradually resumed.

The device can apply tPBM to DMN, occipital lobe as well as to Broca and Wernike areas. The device will collect EEG from prefrontal cortex, occipital cortex and temporal cortex (left and right to monitor hemispheric dominance observed in ASD children). The platform connected to the device can conduct initial assessment of behavioral symptoms (to be correlated with EEG data) as well as ongoing collection of symptoms (allowing for continuous correlations with EEG). Therefore the platform will continuously measure the efficacy of tPBM.

The process flow diagram in FIG. 14 illustrates the method 500 of performing transcranial illumination in combination with the use of one or more sensors to measure characteristics of the brain to monitor the treatment and detect changes in tissue that indicate a response during one or more sessions. Preferred embodiments can utilize an EEG sensor array with the head wearable device to measure brain electric field conditions where manual or preset parameters are selected 502 for a therapeutic session. The system performs transcranial illumination 504 and data is recorded such as EEG sensor data. Depending on the measured data and condition of the patient, the system can automatically adjust operating parameters or they can be manually adjusted 506 by the clinician. The data can be communicated 508 to the computing device such as the control tablet device and stored in the electronic medical record of the patient. This can be transmitted by communication networks to a hospital or clinic server for storage and further analysis as described herein. Shown in FIG. 15 is a table with exemplary values for illumination conditions that can be employed by the system. These parameters typically fall within a range of values that the system can use that extend between a minimum threshold and a maximum threshold. These thresholds can be age dependent as the thickness and density of the cranium of a child increase with age as described in Smith et al, "Automated Measurement of Cranial Bone Thickness and Density from Clinical Computed Tomography," IEEE conference proceedings Eng Med Biol Soc. 2012:4462-4465 (EMBC 2012), the entire contents of which is incorporated herein by reference. Thus, an age dependent quantitative rating can be associated with each patient that is used to define the illumination parameters used for that patient. Note that different lobes of a child may increase in thickness and/or density at different rates over time. Thus, the power density to be delivered to a child at age 4 will be less than that used for a 5 or 6 year old, for example.

Figure 16:
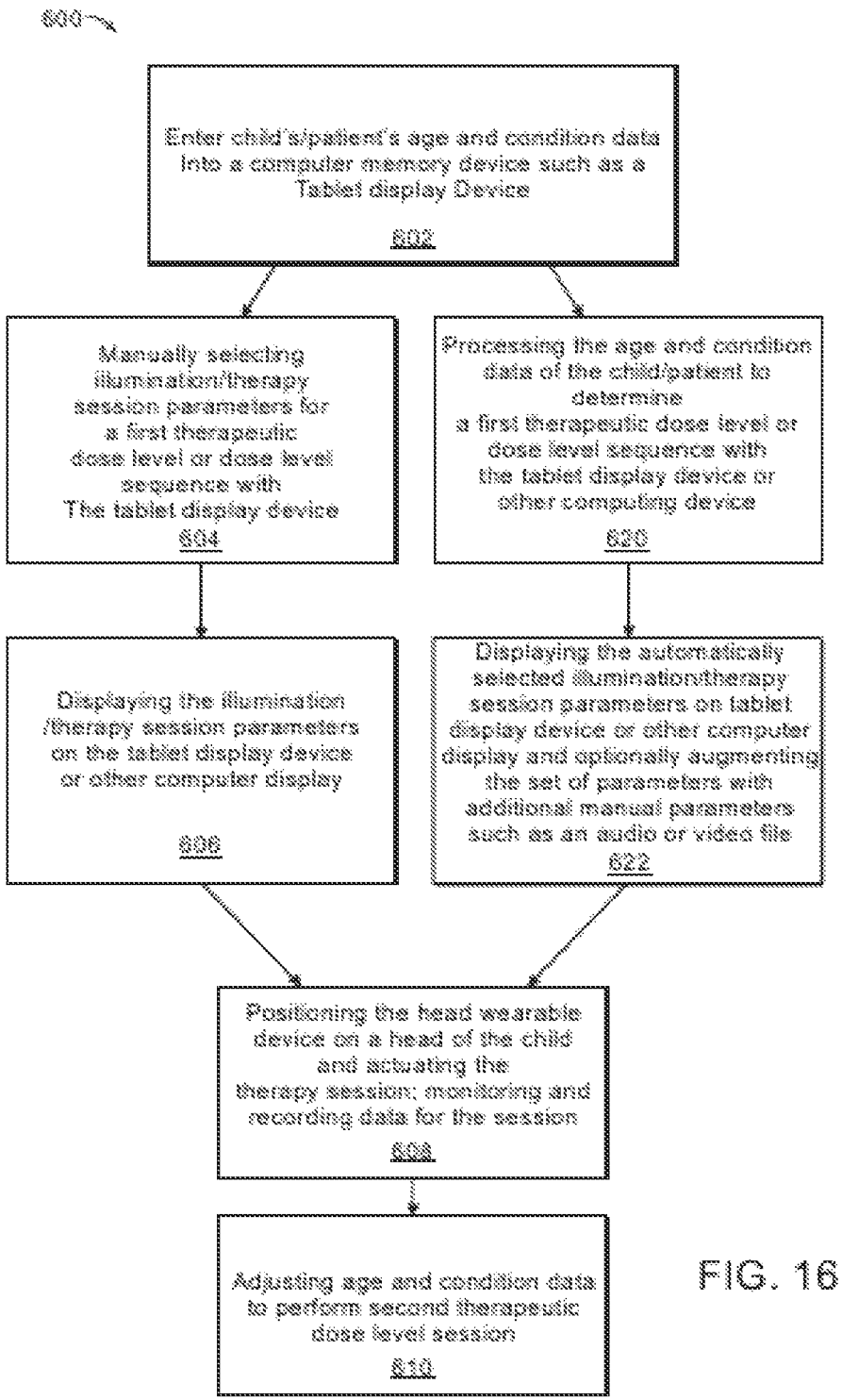
FIG. 16 illustrates a process flow diagram for selecting and optimizing parameters over multiple therapeutic sessions including manual and automated selection tracks.

Thus, an operating module of the software can be programmed to retrieve fields of data or data files from a patient data entry module that can include patient information and other initial observations of parents or clinicians regarding a child's age, condition, medical history including medications that may impact a further diagnostic or therapeutic program. FIG. 16 illustrates a process flow diagram for a method 600 of selecting and optimizing parameters over multiple therapeutic sessions including manual and automated selection tracks. Initially, patient data related to a child or adult patient (such as age or condition) can be entered by a user into a memory of a computing device (step 602). For example, data can be entered by a user through the GUI 160 of the remote computing device 150 (such as a tablet computing device) and stored in the memory 156 as described previously in relation to FIG. 4. The method 600 can then follow one of two tracks. In one embodiment, the user can manually select illumination or therapy session parameters for a first therapeutic dose level or dose level sequence based upon the patient data (step 604). For example, the user can manually select parameters from menu or other displays on the GUI 160 of the remote computing device 150. Then, the illumination and/or therapy session parameters (which may include user-selected parameters and other parameters whether automatically determined or set by default) can be displayed on the computer display (step 606). For example, the parameters can be displayed on the visual display device 152. The device can also be programmed to operate a linguistic and/or visual message therapy module that communicates auditory and/or visual messages to the patient during a therapy session.

In an alternative embodiment, the parameters can be set algorithmically or automatedly. The processor of the computing device can process the patient data (including, for example, age and condition data) to determine the first therapeutic dose level or dose level sequence (step 620). For example, the processor 155 of the remote computing device 150 can analyze and process the patient data. Then, the automatically selected illumination and therapy session parameters (as well as other session parameters) can be displayed on the display associated with the computing device (step 622). Optionally, the set of automatically selected parameters can be augmented in this step with additional manual parameters such as an audio or video file used as part of the therapeutic session.

Whether the parameters are determined automatically or manually, the head wearable device can then be positioned on the head of patient (e.g., a child or adult) and the therapy session can be actuated based on the session parameters (step 608). Data related to the patient or device during the session can be monitored and recorded. Then, the patient data (e.g., age or condition data) can be adjusted to optimize session parameters for future (i.e., second, third, or more) therapeutic sessions (step 610).

Figure 17:
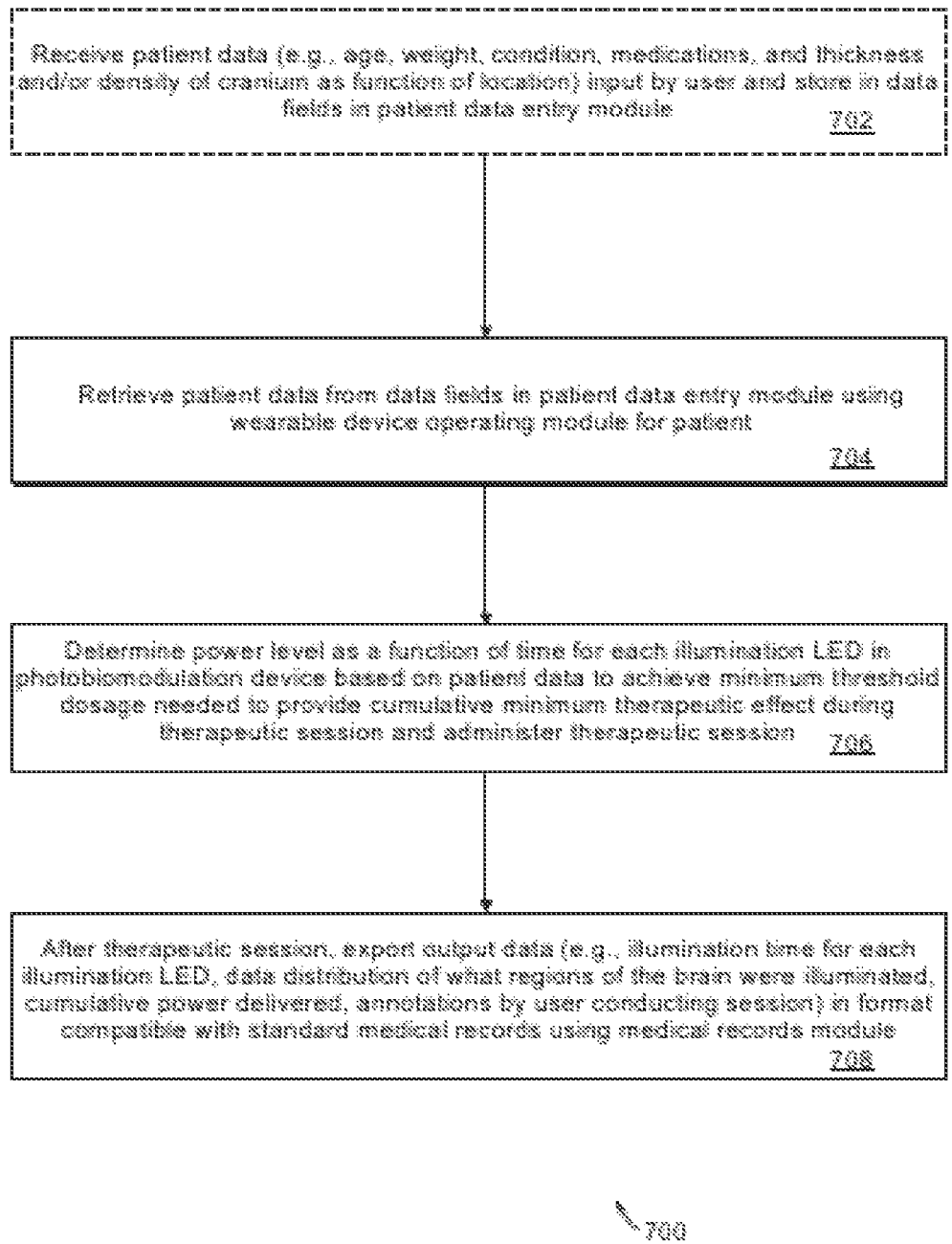
FIG. 17 illustrates a process flow diagram for administering a therapeutic session to a patient in accordance with various embodiments described herein.

FIG. 17 illustrates a process flow diagram for a method 700 for administering a therapeutic session to a patient in accordance with various embodiments described herein. As an optional first step, patient data can be input by a user to a computing device and stored in data fields in a patient data entry module resident in the computing device or a server device (step 702). Relevant patient data entered in this step can include patient age, weight, physical or mental condition, medication history or regimen, and a data map of cranial thickness or density as a function of location on the patient's cranium. For example, the patient data entry module can reside in the memory 156 of the remote computing device 150, and patient data can be entered using the GUI 160 such as by using a keyboard, mouse, or multi-point touch interface 420. This step may be considered optional as the patient data for a particular patient may already be resident in patient data entry module (e.g., the data may have been entered during previous sessions and need not be re-entered). The patient data is then retrieved from the data fields in the patient data entry module using the wearable device operating module (step 704). The wearable device operating module can determine a power level as a function of time for each illumination LED 115a-115e in the array of the photobiomodulation device 110 based on the patient data to achieve the minimum therapeutic effect during the therapeutic session. Once the power levels are determined, the therapeutic session can be administered to the patient (step 706).

After concluding the therapeutic session, output data can be exported in a format compatible with standard medical records using a medical records module (step 708). Output data can include the illumination time and/or power for each individual illumination LED, a data distribution of which regions of the brain were illuminated, the cumulative power delivered, or annotations from a user conducting the session such as a medical professional. The data can be time-course data including time stamps that record when observations or other data events occurred within the therapeutic session.

Figure 18:
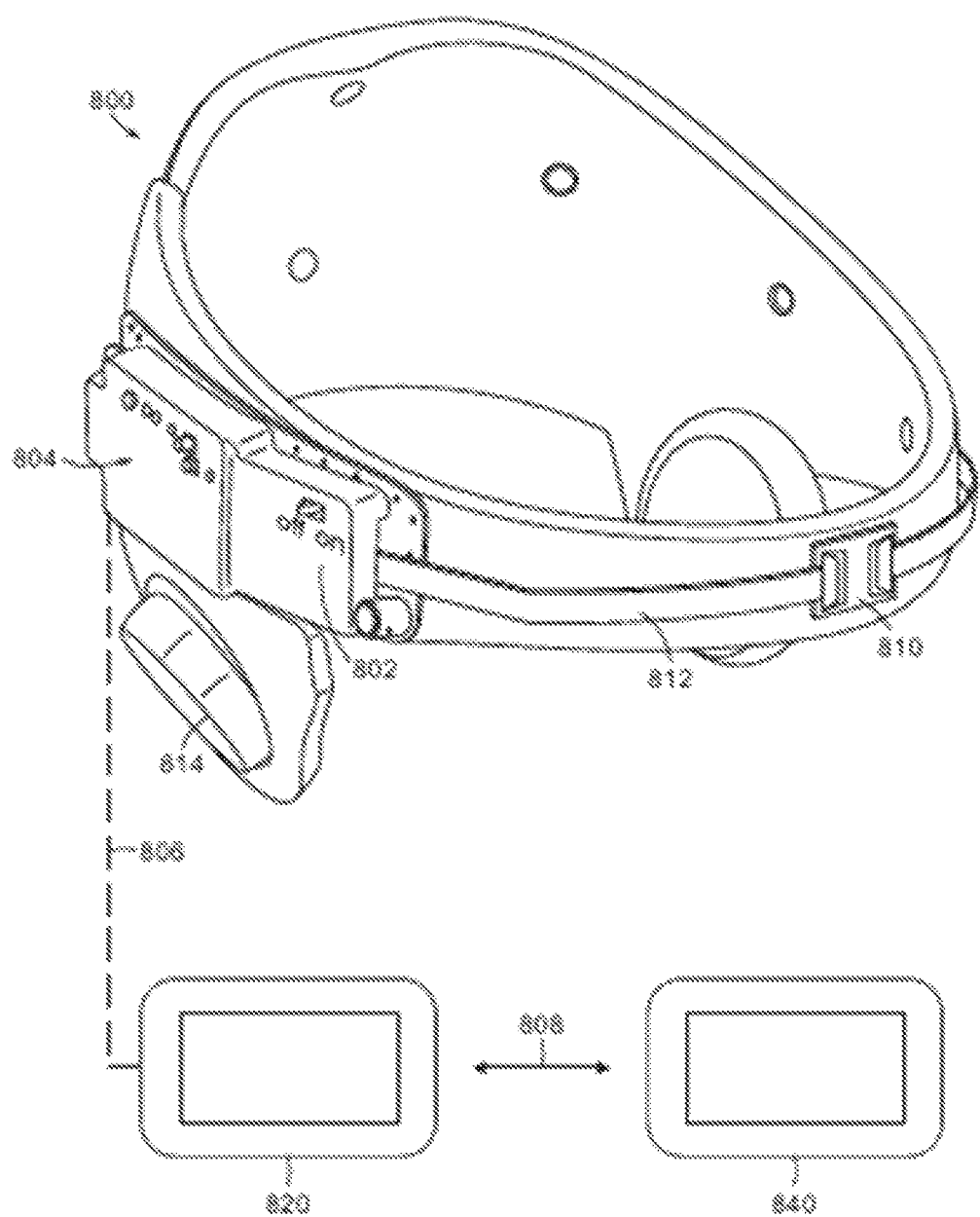
FIG. 18 illustrates a further view of a head worn device having circuit housing elements accessible to a user that is communicably connected to a first tablet device used by the patient during a therapy session and a second tablet used by an operator to monitor, control and/or program the system for diagnostic and therapeutic use as described generally herein.

Shown in FIG. 18 is a further implementation in which the head wearable device 800 has light emitting devices 810 at spaced locations around the head of the patient connected by a cable 812 to a circuit housing having a first portion with an on/off switch 802 and a second portion with one or more control buttons or actuators 804 to manually select operating modes of the device as described herein. Headphone speakers and/or microphones 814 can be mounted to the head worn device 800 or speakers/microphones can alternatively be within a first tablet 820 that can be used by the patient during a therapy session. The first tablet or mobile phone 820 can be connected by wire or cable 806 to device 800 and can emit sounds or auditory signals for improving linguistic skills of the patient as described herein. The display on the first tablet can also be used to display images or video to the patient during the therapy session. A second tablet or mobile phone 840 can also communicate with the head worn device 800 and/or the first tablet by a cable or wireless connection 808. Tablet 840 can be used by an operating user to control operation of one or both of the head worn device 800 and first tablet 820, before, during or after a therapy session. For example, if an EEG sensor is used during a therapy session, this can serve to monitor the procedure or calibrate the power level to be used on a particular patient to establish the minimum level therapeutic dose, and optionally to also set a maximum dose for each period of illumination during the session, and further optionally to select which regions of the brain of the patient are to be illuminated during a session. The first tablet may be programmed only to provide the auditory and/or visual components to the patient, whereas the second tablet can be programmed solely for use by the operator or clinician to manage the therapy provided to one or more patients in separate sessions.

Throughout the specification and the claims, the following terms take at least the meanings explicitly associated herein, unless the context clearly dictates otherwise. The term "or" is intended to mean an inclusive "or." Further, the terms "a," "an," and "the" are intended to mean one or more unless specified otherwise or clear from the context to be directed to a singular form.

In this description, numerous specific details have been set forth. It is to be understood, however, that implementations of the disclosed technology can be practiced without these specific details. In other instances, well-known methods, structures and techniques have not been shown in detail in order not to obscure an understanding of this description. References to "one embodiment," "an embodiment," "some embodiments," "example embodiment." "various embodiments." "one implementation," "an implementation," "example implementation," "various implementations." "some implementations." etc., indicate that the implementation(s) of the disclosed technology so described can include a particular feature, structure, or characteristic, but not every implementation necessarily includes the particular feature, structure, or characteristic. Further, repeated use of the phrase "in one implementation" does not necessarily refer to the same implementation, although it can.

As used herein, unless otherwise specified the use of the ordinal adjectives "first." "second." "third," etc., to describe a common object, merely indicate that different instances of like objects are being referred to, and are not intended to imply that the objects so described must be in a given sequence, either temporally, spatially, in ranking, or in any other manner.

While certain implementations of the disclosed technology have been described in connection with what is presently considered to be the most practical and various implementations, it is to be understood that the disclosed technology is not to be limited to the disclosed implementations, but on the contrary, is intended to cover various modifications and equivalent arrangements included within the scope of the appended claims. Although specific terms are employed herein, they are used in a generic and descriptive sense only and not for purposes of limitation.

This written description uses examples to disclose certain implementations of the disclosed technology, including the best mode, and also to enable any person skilled in the art to practice certain implementations of the disclosed technology, including making and using any devices or systems and performing any incorporated methods. The patentable scope of certain implementations of the disclosed technology is defined in the claims, and can include other examples that occur to those skilled in the art. Such other examples are intended to be within the scope of the claims if they have structural elements that do not differ from the literal language of the claims, or if they include equivalent structural elements with insubstantial differences from the literal language of the claims.

Exemplary flowcharts are provided herein for illustrative purposes and are non-limiting examples of methods. One of ordinary skill in the art will recognize that exemplary methods may include more or fewer steps than those illustrated in the exemplary flowcharts, and that the steps in the exemplary flowcharts may be performed in a different order than the order shown in the illustrative flowcharts.

The invention claimed is:

1. A photobiomodulation neuro-therapy device comprising:
a portable head mounted device that is sized to be positioned on a patient's head, the portable head mounted device including a plurality of light emitting devices, a memory and a battery providing power to the portable head mounted device, each of the light emitting devices being operable in response to control signals to control emission of transcranial illuminating light into the patient having a near infrared wavelength delivered during a therapeutic period;
a processor mounted on the portable head mounted device, the processor being connected to each of the light emitting devices to execute instructions to communicate the control signals that individually control emission of illuminating light from each of the light emitting devices during the therapeutic period;
a sensor that measures a physiologic response of the patient, the sensor including an electroencephalogram (EEG) electrode device that measures a brain wave signal of the patient wherein the EEG electrode device communicates measured EEG signals to at least one of the processor mounted on the portable head mounted device and an external communication device; and
a wireless receiver mounted on the portable head mounted device that receives wireless signals from the external communication device programmed to transmit therapeutic parameters to the processor mounted on the portable head mounted device.

2. The device of claim 1 wherein the memory records an amount of the transmitted light delivered to the patient during the therapeutic period.

3. The device of claim 1 wherein the external communication device comprises a portable display device having a processing device, a graphical user interface and a portable display device memory that stores a plurality of programmed modules configured to control one or more operations of the portable head mounted device, the processing device executing a software program that operates the portable head mounted device.

4. The device of claim 1 wherein the plurality of light emitting devices further comprise a first light emitter that illuminates the patient at a first wavelength and a second light emitter that illuminates the patient at a second wavelength different than the first wavelength.

5. The device of claim 1 wherein the plurality of light emitting devices further comprise a plurality of panels that illuminate the cranium of the patient with the illuminating light from a plurality of different angles, each panel having one or more light emitting diodes (LEDs) that illuminates the cranium with at least one of a frontal lobe light emitting panel, an occipital lobe light emitting panel and a side light emitting panel that are mounted on the portable head mounted device.

6. The device of claim 5 wherein each panel in the plurality of panels comprises an LED circuit board on which the at least one light emitting diode is mounted, each LED circuit board being connected to a power control circuit mounted on a rear portion of the portable head mounted device, at least one LED being positioned on the portable head mounted device to transmit light through the cranium into a frontal lobe, at least a second LED being positioned on the portable head mounted device to transmit light through the cranium into a temporal lobe, and at least a third LED on the portable head mounted device to transmit light through the cranium and into the occipital lobe.

7. The device of claim 6 wherein the battery is connected to the power control circuit mounted on a controller circuit board, the battery being attached to a battery holder on the portable head mounted device such that the battery in the battery holder can be replaced.

8. The device of claim 1 further comprising a device sensor that measures an operating condition of the device wherein the processor, in response to a sensed value from the device sensor, controls an operation of the portable head mounted device.

9. The device of claim 8 wherein the processor, in response to sensed data, operates to control power distribution to each of the light emitting devices.

10. The device of claim 1 wherein the wireless receiver comprises a transceiver such that the transceiver transmits data stored in the memory on the portable head mounted device to the external communication device that stores patient data for each therapeutic session.

11. The device of claim 10 wherein the external communication device comprises a user interface that controls an operation of the portable head mounted device and wherein the external communication device receives measured EEG signals from the EEG electrode device and transmits a control signal to the processor on the portable head mounted device to adjust an operation.

12. The device of claim 1 wherein the portable head mounted device has a size, shape and weight to be worn by a child, and wherein the processor is programmed to treat a neurological condition that comprises autism.

13. The device of claim 1 further comprising a graphical user interface is operable on the touchscreen display that is responsive to a plurality of touch gestures whereby a user can control one or more operating parameters of the portable head mounted device.

14. The device of claim 1 wherein the external communication device can be selectively connected to the head wearable device with a cable.

15. The device of claim 1 wherein the external communication device comprises a tablet display device having a touchscreen display that is operative in response to a plurality of touch gestures made by a user on the surface of the touchscreen display, the tablet display device including a tablet display device processor programmed with one or more software modules to control operations of the tablet display device and the portable head mounted device.

16. The device of claim 1 wherein each light emitting device can be adjusted to different positions on the portable head mounted device and the total power emitted by each light emitting device can be incremented between different power levels.

17. The device of claim 1 wherein the light emitting devices operate in response to programmed instructions such that the processor executes a sequence of steps to illuminate different regions of brain tissue of the patient with selected levels of light.

18. The device of claim 17 wherein the selected levels of light comprise a plurality of presets such that a user can select at least one preset that includes a time duration, a total area of a cranium of the patient to be automatically illuminated and a total amount of light to be delivered through the total area of the cranium of the patient during the therapeutic session.

19. The device of claim 17 wherein the selected levels of light are manually selected by a user of the external communication device with a user interface on the external communication device.

20. The device of claim 1 wherein the EEG electrode device is mounted on the portable head mounted device and connected to the processor, the measured EEG signals being stored in the memory.

* * * * *